(12) United States Patent
Xia et al.

(10) Patent No.: US 10,519,150 B2
(45) Date of Patent: Dec. 31, 2019

(54) SALTS OF MORPHOLINE DERIVATIVE, CRYSTAL FORMS THEREOF, PROCESSES FOR PRODUCING THE SAME, PHARMACEUTICAL COMPOSITIONS INCLUDING THE SAME, AND USE THEREOF

(71) Applicant: SHANGHAI PHARMACEUTICALS HOLDING CO., LTD., Shanghai (CN)

(72) Inventors: Guangxin Xia, Shanghai (CN); Jianshu Xie, Shanghai (CN); Guohui Jia, Shanghai (CN); Jiansheng Han, Shanghai (CN); Naoko Ueda, Osaka (JP); Toru Iijima, Osaka (JP)

(73) Assignee: SHANGHAI PHARMACEUTICALS HOLDING CO., LTD., Shanghai (CN)

( * ) Notice: Subject to any disclaimer, the term of this patent is extended or adjusted under 35 U.S.C. 154(b) by 0 days.

(21) Appl. No.: 16/066,490

(22) PCT Filed: Dec. 29, 2016

(86) PCT No.: PCT/CN2016/112966
§ 371 (c)(1),
(2) Date: Jun. 27, 2018

(87) PCT Pub. No.: WO2017/114456
PCT Pub. Date: Jul. 6, 2017

(65) Prior Publication Data
US 2019/0016718 A1   Jan. 17, 2019

(30) Foreign Application Priority Data

Dec. 29, 2015 (CN) .......................... 2015 1 1016783

(51) Int. Cl.
| | |
|---|---|
| C07D 471/04 | (2006.01) |
| A61K 31/5377 | (2006.01) |
| C07C 51/41 | (2006.01) |
| C07C 53/10 | (2006.01) |
| C07C 59/245 | (2006.01) |
| C07C 59/255 | (2006.01) |
| C07C 309/35 | (2006.01) |
| C07C 51/43 | (2006.01) |

(52) U.S. Cl.
CPC ........ *C07D 471/04* (2013.01); *A61K 31/5377* (2013.01); *C07C 51/41* (2013.01); *C07C 51/43* (2013.01); *C07C 53/10* (2013.01); *C07C 59/245* (2013.01); *C07C 59/255* (2013.01); *C07C 309/35* (2013.01); *C07B 2200/13* (2013.01)

(58) Field of Classification Search
CPC .. C07D 471/04; A61K 31/5377; C07C 51/41; C07C 51/43; C07C 53/10; C07C 59/245; C07C 59/255; C07C 309/35; C07B 2200/13
See application file for complete search history.

(56) References Cited

U.S. PATENT DOCUMENTS

2014/0011807 A1* 1/2014 Iijima .................. C07D 265/30
514/234.5

FOREIGN PATENT DOCUMENTS

| CN | 103562191 A | 2/2014 |
| WO | WO 2012/124775 A1 | 2/2014 |

OTHER PUBLICATIONS

Berge, S.M., et al, "Pharmaceutical Salts," Journal of Pharmaceutical Sciences, Jan. 31, 1977 vol. 66, No. 1, pp. 1-19.
English translation of International Preliminary Report on Patentabillty for Appl. No. PCT/CN2016/112966 dated Jul. 3, 2018.
English translation of International Search Report for Appl. No. PCT/CN2016/112966 dated Mar. 16, 2017

* cited by examiner

*Primary Examiner* — Timothy R Rozof
(74) *Attorney, Agent, or Firm* — Birch, Stewart, Kolasch & Birch, LLP

(57) ABSTRACT

The present invention provides novel pharmaceutically acceptable salts of a morpholine derivative, including a malate, a tartrate, a hydrochloride, an acetate, and a naphthalene disulfonate thereof, wherein the tartrate has 3 crystal salt forms: crystal form A, crystal form B and dihydrate; the malate, the hydrochloride, and the acetate each have one crystal salt form; the naphthalene disulfonate is amorphous. When compared to the known morpholine derivative free base, the present invention has one or more improved properties, e.g., a better crystalline state, greatly improved water solubility, light stability and thermal stability, etc. The present invention further provides preparation methods for the salts of morpholine derivative and the crystal forms thereof, pharmaceutical compositions and use thereof.

16 Claims, 30 Drawing Sheets

SALTS OF MORPHOLINE DERIVATIVE, CRYSTAL FORMS THEREOF, PROCESSES FOR PRODUCING THE SAME, PHARMACEUTICAL COMPOSITIONS INCLUDING THE SAME, AND USE THEREOF

TECHNICAL FIELD

The invention belongs to pharmaceutical chemistry field, in particular relates to salts of a morpholine derivative, and crystal forms thereof, processes for producing the same, pharmaceutical compositions including the same, and use thereof.

BACKGROUND ART

A morpholine derivative, chemical name: methyl (3-(3-((R)-1-((R)—N-cyclopropylmorpholine-2-carboxamido)ethyl)-6-methyl-1H-pyrazolo[3,4-b]pyridin-1-yl)n-propyl)carbamate, molecular formula: $C_{22}H_{32}N_6O_4$, has the following structural formula:

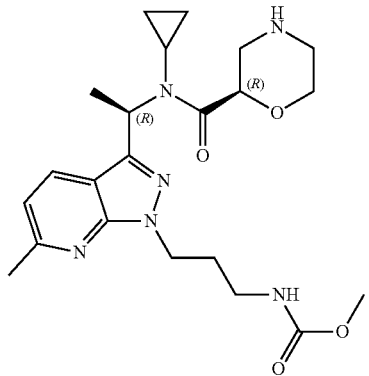

CN103562191 (201280013626.5) discloses a free base form of the morpholine derivative, its preparation method and its renin inhibitory activity. The free base is a semi-solid or amorphous powder and shows poor water solubility, and it is relatively easy to be oxidized and thus not suitable for long-term storage.

CONTENT OF THE INVENTION

In view of the defects in the prior art, the present invention provides novel pharmaceutically acceptable salts of morpholine derivative, including a malate, a tartrate, a hydrochloride, an acetate, and a naphthalene disulfonate thereof, wherein the tartrate has 3 crystal salt forms: crystal form A (tetrahydrate), crystal form B (anhydrous form) and dihydrate; the malate, the hydrochloride, and the acetate each have one crystal salt form; the naphthalene disulfonate is amorphous. The present invention has one or more improved properties compared to the known morpholine derivative free base. The present invention further provides preparation methods for the salts of morpholine derivative and the crystal forms thereof, pharmaceutical compositions and use thereof.

In one aspect, the present invention provides a morpholine derivative malate and a process for producing the same.

The morpholine derivative malate is a compound formed by the morpholine derivative and L-malic acid in a molar ratio of 1:1, and represented by the following structural formula:

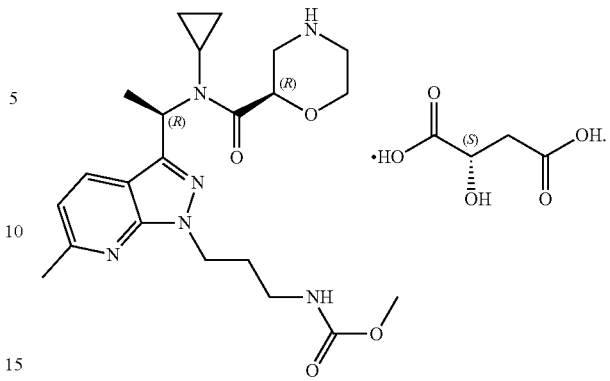

The morpholine derivative malate has a crystal form having characteristic peaks at 2θ of 7.767°±0.2°, 13.897°±0.2°, 14.775°±0.2°, 17.098°±0.2°, 18.999°±0.2°, 20.153±0.2°, 20.960°±0.2°, 21.423°±0.2°, 26.348°±0.2°, 27.892°±0.2° in the X-ray powder diffraction pattern.

Preferably, the morpholine derivative malate crystal form has characteristic peaks at 2θ of 5.598°±0.2°, 7.357°±0.2°, 7.767°±0.2°, 10.395°±0.2°, 11.108°±0.2°, 13.897°±0.2°, 14.775°±0.2°, 16.037°±0.2°, 16.523°±0.2°, 17.098°±0.2°, 18.999°±0.2°, 19.410°±0.2°, 20.153°±0.2°, 20.960°±0.2°, 21.423°±0.2°, 22.645°±0.2°, 26.348°±0.2°, 26.630°±0.2°, 26.891°±0.2°, 27.380°±0.2°, 27.892°±0.2°, 31.056°±0.2°, 33.306°±0.2°, 33.775°±0.2°, 39.231°±0.2° in the X-ray powder diffraction pattern.

Further, the morpholine derivative malate exhibits an X-ray Powder Diffraction (XRPD) pattern as shown in FIG. 1.

Further, the morpholine derivative malate exhibits a Polarized Light Microscopy (PLM) image as shown in FIG. 2.

Further, the morpholine derivative malate exhibits a Thermogravimetric Analysis (TGA) plot as shown in FIG. 3, the TGA plot shows that the morpholine derivative malate is decomposed at about 185.8° C., and the sample loses no weight before decomposition.

Further, the morpholine derivative malate exhibits a Differential Scanning Calorimetry (DSC) plot as shown in FIG. 4, and the DSC plot shows an endothermic peak (95 J/g) at about 121° C.

Further, the morpholine derivative malate exhibits a Dynamic Vapor Sorption Analysis (DVS) plot as shown in FIG. 5, and the DVS plot shows that the weight of the morpholine derivative malate changes for about 1.2% in a range of 20%-80% humidity.

The method for preparing the morpholine derivative malate comprises the following steps: dissolving the morpholine derivative free base in acetone, chloroform, acetonitrile, ethyl acetate, methanol or tetrahydrofuran (preferably acetone) to obtain a solution of the morpholine derivative free base in acetone, chloroform, acetonitrile, ethyl acetate, methanol or tetrahydrofuran, dissolving L-malic acid in ethanol to obtain a solution of L-malic acid in ethanol, dropwisely adding the solution of L-malic acid in ethanol into the solution of the morpholine derivative free base in acetone, chloroform, acetonitrile, ethyl acetate, methanol or tetrahydrofuran, stirring overnight at room temperature to precipitate a white solid, and filtering. Preferably, the molar ratio of the morpholine derivative free base to malic acid is 1:1.1 to 1:3.3, preferably 1:1.1.

Compared with the prior art, the morpholine derivative malate has one or more improved properties, e.g., it has a better crystalline state, it is hardly hygroscopic in 20%-80% RH, meanwhile, the water solubility is greatly improved (~100 mg/mL), and it has better stability under light and oxidation conditions.

In the second aspect, the present invention provides a morpholine derivative tartrate and its crystal form, and a process for producing the same.

The morpholine derivative tartrate is a compound formed by the morpholine derivative and L-tartaric acid in a molar ratio of 1:1, and represented by the following structural formula:

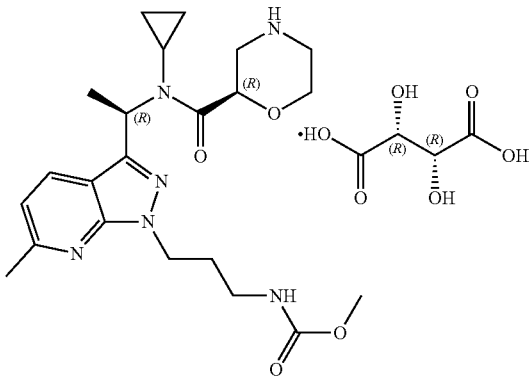

The preparation method of the morpholine derivative tartrate comprises the following steps: dissolving the morpholine derivative free base in acetone, chloroform, acetonitrile, ethyl acetate, methanol or tetrahydrofuran (preferably acetone), dissolving L-tartaric acid in water, dropwisely adding the aqueous solution of L-tartaric acid into the solution of the morpholine derivative free base in acetone, chloroform, acetonitrile, ethyl acetate, methanol, or tetrahydrofuran, stirring overnight at room temperature to precipitate a white solid, and filtering.

The molar ratio of the morpholine derivative to L-tartaric acid is 1:1.03 to 1:2.2, preferably 1:1.03.

The morpholine derivative tartrate is a morpholine derivative tartrate crystal form B, which has characteristic peaks at 2θ of 3.339°±0.2°, 6.562°±0.2°, 11.331°±0.2°, 16.396°±0.2°, 22.041°±0.2° in the X-ray powder diffraction pattern.

Preferably, the morpholine derivative tartrate crystal form B has characteristic peaks at 2θ of 3.339°±0.2°, 5.078°±0.2°, 6.562°±0.2°, 6.864°±0.2°, 8.250°±0.2°, 8.444°±0.2°, 11.030°±0.2°, 11.331°±0.2°, 12.864°±0.2°, 13.907°±0.2°, 14.642°±0.2°, 16.396°±0.2°, 19.100°±0.2°, 19.359°±0.2°, 22.041°±0.2°, 25.251°±0.2°, 26.768°±0.2°, 27.894°±0.2°, 29.510°±0.2°, 38.343°±0.2° in the X-ray powder diffraction pattern.

Further, the morpholine derivative tartrate crystal form B exhibits an XRPD pattern as shown in FIG. 6.

Further, the morpholine derivative tartrate crystal form B exhibits a PLM image as shown in FIG. 7.

Further, the morpholine derivative tartrate crystal form B exhibits a TGA plot as shown in FIG. 8, the TGA plot shows that the morpholine derivative tartrate crystal form B is decomposed at about 186.0° C., and 2.5% of the weight is slowly lost before decomposition (the weight begins to lose at about 150° C.).

Further, the morpholine derivative tartrate crystal form B exhibits a DSC plot as shown in FIG. 9, and the DSC plot shows that the morpholine derivative tartrate crystal form B has an endothermic peak (38 J/g) at about 161.5° C.

Further, the morpholine derivative tartrate crystal form B exhibits a DVS plot as shown in FIG. 10, and the DVS plot shows that the weight change is about 7% in a range of 20%-80% humidity, it is relatively hydroscopic, and may become a hydrate.

The morpholine derivative tartrate crystal form B is added to a mixed solvent of acetone and water, the mixture is stirred for 2 days at room temperature, and then filtered to obtain a morpholine derivative tartrate dihydrate; the volume ratio of acetone to water is preferably 30:1.

The morpholine derivative tartrate dihydrate has a crystal form having characteristic peaks at 2θ of 9.851°±0.2°, 14.410°±0.2°, 14.774°±0.2°, 15.052°±0.2°, 16.254°±0.2°, 20.847°±0.2°, 23.225°±0.2° in the X-ray powder diffraction pattern.

Preferably, the crystal form of the morpholine derivative tartrate dihydrate has characteristic peaks at 2θ of 9.851°±0.2°, 13.434°±0.2°, 14.410°±0.2°, 14.774°±0.2°, 15.052°±0.2°, 15.415°±0.2°, 15.701°±0.2°, 16.254°±0.2°, 16.755°±0.2°, 17.283°±0.2°, 18.079°±0.2°, 18.576°±0.2°, 20.077°±0.2°, 20.847°±0.2°, 21.960°±0.2°, 23.225°±0.2°, 24.351°±0.2°, 27.046°±0.2°, 27.865°±0.2°, 38.458°±0.2° in the X-ray powder diffraction pattern.

Further, the morpholine derivative tartrate dihydrate exhibits an XRPD pattern as shown in FIG. 11.

Further, the morpholine derivative tartrate dihydrate exhibits a PLM image as shown in FIG. 12.

Further, the morpholine derivative tartrate dihydrate exhibits a TGA plot as shown in FIG. 13, the TGA plot shows that the morpholine derivative tartrate dihydrate is decomposed at about 189.6° C., and 6.95% of its weight is gradiently lost before decomposition.

Further, the morpholine derivative tartrate dihydrate exhibits a DSC plot as shown in FIG. 14, and the DSC plot shows that the morpholine derivative tartrate dihydrate has an endothermic peak (112 J/g) at about 29.5° C., an exothermic peak (27 J/g) at about 99° C. and an endothermic peak (19 J/g) at about 154° C.

Further, the morpholine derivative tartrate dihydrate exhibits a DVS plot as shown in FIG. 15, and the DVS plot shows that the weight change is about 11.06% in a range of 0%-80% humidity, and it is relatively hydroscopic.

The present application further discloses a morpholine derivative tartrate tetrahydrate, which is referred as crystal form A and it has characteristic peaks at 2θ of 9.882°±0.2°, 14.426°±0.2°, 14.802°±0.2°, 16.275°±0.2°, 20.085°±0.2°, 20.872°±0.2°, 21.978°±0.2°, 23.236°±0.2° in the X-ray powder diffraction pattern.

Preferably, the morpholine derivative tartrate crystal form A has characteristic peaks at 2θ of 9.882°±0.2°, 11.964°±0.2°, 13.558°±0.2°, 14.426°±0.2°, 14.802°±0.2°, 15.076°±0.2°, 15.450°±0.2°, 16.046°±0.2°, 16.275°±0.2°, 16.754°±0.2°, 17.320°±0.2°, 18.450°±0.2°, 18.790°±0.2°, 19.728°±0.2°, 20.085°±0.2°, 20.577°±0.2°, 20.872°±0.2°, 21.978°±0.2°, 22.426°±0.2°, 23.236°±0.2°, 23.704°±0.2°, 24.399°±0.2°, 25.346°±0.2°, 25.913°±0.2°, 26.991°±0.2°, 28.199°±0.2°, 28.445°±0.2°, 29.030°±0.2°, 30.209°±0.2°, 30.480°±0.2°, 32.791°±0.2°, 34.796°±0.2°, 36.226°±0.2°, 38.472°±0.2° in the X-ray powder diffraction pattern.

The morpholine derivative tartrate crystal form A exhibits an XRPD pattern as shown in FIG. 16.

The morpholine derivative tartrate crystal form A exhibits a PLM image as shown in FIG. 17.

The morpholine derivative tartrate crystal form A exhibits a TGA plot as shown in FIG. 18.

The morpholine derivative tartrate crystal form A exhibits a DSC plot as shown in FIG. 19.

The morpholine derivative tartrate crystal form A exhibits a DVS plot as shown in FIG. 20.

The present application further discloses a preparation method for the morpholine derivative tartrate crystal form A, comprising the following steps: dissolving the morpholine derivative free base in acetone, chloroform, acetonitrile, ethyl acetate, methanol or tetrahydrofuran (preferably acetone) to obtain a solution of the morpholine derivative free base in acetone, chloroform, acetonitrile, ethyl acetate, methanol or tetrahydrofuran, dissolving L-tartaric acid in water to obtain an aqueous solution of tartaric acid, dropwisely adding the aqueous solution of L-tartaric acid into the solution of the morpholine derivative free base in acetone, chloroform, acetonitrile, ethyl acetate, methanol or tetrahydrofuran, stirring at room temperature for not less than 48 hours to precipitate a white solid, and filtering. The molar ratio of the morpholine derivative free base to L-tartaric acid is 1:2.2, the volume ratio of acetone to water is 20:1.

Compared with the prior art, the morpholine derivative tartrate has one or more improved properties, e.g., both of the crystal forms A and B have better crystalline states, but the crystal form A is hardly hydroscopic, while crystal form B is relatively hydroscopic in 20%-80% RH, the water solubility thereof is improved (50-300 mg/mL), and crystal form B is more stable than crystal form A under oxidation condition, while both have equivalent stability under light condition.

In the third aspect, the present invention provides a morpholine derivative hydrochloride and a process for producing the same.

The morpholine derivative hydrochloride is a compound formed by the morpholine derivative and hydrochloric acid in a molar ratio of 1:2, and represented by the following structural formula:

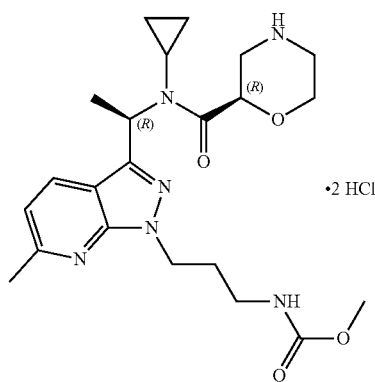

The morpholine derivative hydrochloride has a crystal form having characteristic peaks at 2θ of 3.981°±0.2°, 7.784°±0.2°, 8.667°±0.2°, 13.634°±0.2°, 18.238°±0.2°, 19.620°±0.2°, 24.624°±0.2°, 24.987°±0.2°, 28.072°±0.2°, 31.815°±0.2° in the X-ray powder diffraction pattern.

Preferably, the morpholine derivative hydrochloride crystal form has characteristic peaks at 2θ of 3.981°±0.2°, 7.784°±0.2°, 8.667°±0.2°, 10.914°±0.2°, 11.557°±0.2°, 12.211°±0.2°, 13.634°±0.2°, 14.675°±0.2°, 15.419°±0.2°, 15.817°±0.2°, 17.158°±0.2°, 18.238°±0.2°, 19.116°±0.2°, 19.620°±0.2°, 20.618°±0.2°, 21.261°±0.2°, 21.901°±0.2°, 22.428°±0.2°, 22.548°±0.2°, 23.342°±0.2°, 24.624°±0.2°, 24.987°±0.2°, 25.902°±0.2°, 26.267°±0.2°, 26.730°±0.2°, 26.946°±0.2°, 28.072°±0.2°, 29.994°±0.2°, 31.154°±0.2°, 31.815°±0.2°, 33.220°±0.2°, 34.670°±0.2°, 35.201°±0.2° in the X-ray powder diffraction pattern.

Further, the morpholine derivative hydrochloride exhibits an X-ray Powder Diffraction (XRPD) pattern as shown in FIG. 21.

Further, the morpholine derivative hydrochloride exhibits a Polarized Light Microscopy (PLM) image as shown in FIG. 22.

Further, the morpholine derivative hydrochloride exhibits a Thermogravimetric Analysis (TGA) plot as shown in FIG. 23, the TGA plot shows that the morpholine derivative hydrochloride continues to lose weight during the heating process, the decomposition temperature is 207° C. and there are two stages of weight loss before decomposition, and the total weight loss is about 9.1%.

Further, the morpholine derivative hydrochloride exhibits a Differential Scanning Calorimetry (DSC) plot as shown in FIG. 24, and the DSC plot shows a very broad endothermic peak (57.68 J/g) between 25° C. and 115° C., and an endothermic peak (57.65 J/g) at 133° C.

Further, the morpholine derivative hydrochloride exhibits a Dynamic Vapor Sorption Analysis (DVS) plot as shown in FIG. 25, and the DVS plot shows that the morpholine derivative hydrochloride absorbs 15% of water in 0% to 60% RH, and it is deliquescent in this humidity range.

The method for preparing the morpholine derivative hydrochloride comprises the following steps: dissolving the morpholine derivative free base in acetone, chloroform, acetonitrile, ethyl acetate, methanol or tetrahydrofuran (preferably acetone) to obtain a solution of the morpholine derivative free base in acetone, chloroform, acetonitrile, ethyl acetate, methanol or tetrahydrofuran, dissolving hydrochloric acid in acetone to obtain a solution of hydrochloric acid in acetone, dropwisely adding the solution of hydrochloric acid in acetone into the solution of the morpholine derivative free base in acetone, chloroform, acetonitrile, ethyl acetate, methanol or tetrahydrofuran, stirring overnight at room temperature to precipitate a white solid and filtering. Preferably, the molar ratio of the morpholine derivative free base to hydrochloric acid is 1:1.03 to 1:3.5, preferably 1:3.4.

Compared with the prior art, the morpholine derivative hydrochloride has one or more improved properties, e.g., it has a better crystalline state and greatly improved water solubility (>500 mg/mL), but it is very hydroscopic, and it has good thermal stability under light condition.

In the fourth aspect, the present invention provides a morpholine derivative acetate and a process for producing the same.

The morpholine derivative acetate is a compound formed by the morpholine derivative and acetic acid in a molar ratio of 1:1, and represented by the following structural formula:

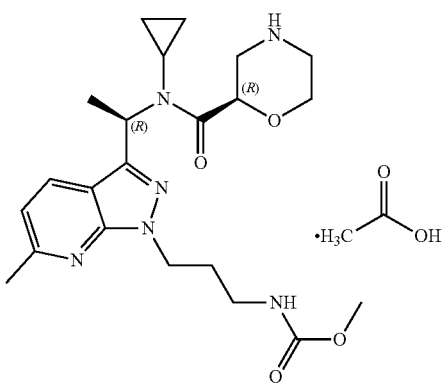

The morpholine derivative acetate has a crystal form having characteristic peaks at 2θ of 7.784°±0.2°, 11.429°±0.2°, 14.455°±0.2°, 16.874°±0.2°, 19.899°±0.2°, 21.146°±0.2°, 24.887°±0.2° in the X-ray powder diffraction pattern.

Preferably, the morpholine derivative acetate crystal form has characteristic peaks at 2θ of 6.012°±0.2°, 7.457°±0.2°, 7.784°±0.2°, 10.391°±0.2°, 10.768°±0.2°, 11.429°±0.2°, 13.652°±0.2°, 14.089°±0.2°, 14.455°±0.2°, 14.841°±0.2°, 15.516°±0.2°, 16.301°±0.2°, 16.874°±0.2°, 17.592°±0.2°, 18.777°±0.2°, 19.375°±0.2°, 19.899°±0.2°, 20.521°±0.2°, 21.146°±0.2°, 21.541°±0.2°, 22.346°±0.2°, 22.966°±0.2°, 23.347°±0.2°, 24.585°±0.2°, 24.887°±0.2°, 25.546°±0.2°, 26.028°±0.2°, 26.328°±0.2°, 27.484°±0.2°, 27.753°±0.2°, 29.206°±0.2°, 30.611°±0.2°, 30.972°±0.2°, 31.233°±0.2°, 31.801°±0.2°, 33.696°±0.2°, 34.699°±0.2°, 35.313°±0.2°, 36.441°±0.2°, 37.961°±0.2°, 38.179°±0.2°, 39.325°±0.2° in the X-ray powder diffraction pattern.

Further, the morpholine derivative acetate exhibits an X-ray Powder Diffraction (XRPD) pattern as shown in FIG. 26.

Further, the morpholine derivative acetate exhibits a Polarized Light Microscopy (PLM) image as shown in FIG. 27.

Further, the morpholine derivative acetate exhibits a Thermogravimetric Analysis (TGA) plot as shown in FIG. 28, the TGA plot shows that the morpholine derivative acetate has a stepwise weight loss of 4.0% and 9.5%, each at about 50° C. and 75° C., respectively.

Further, the morpholine derivative acetate exhibits a Differential Scanning Calorimetry (DSC) plot as shown in FIG. 29, and the DSC plot shows an endothermic peak (61 J/g) at 95° C.

Further, the morpholine derivative acetate exhibits a Dynamic Vapor Sorption Analysis (DVS) plot as shown in FIG. 30, and the DVS plot shows that the morpholine derivative acetate loses about 5% of the weight during the drying stage at 0% of the initial humidity, and then it absorbs moisture in an amount of 6.4% of its weight in a range of 20% to 60% humidity, and absorbs moisture in an amount of 40% of its weight at 90% of humidity, indicating that it is deliquesced.

The method for preparing the morpholine derivative acetate comprises the following steps: dissolving the morpholine derivative free base in acetone, chloroform, acetonitrile, ethyl acetate, methanol or tetrahydrofuran (preferably acetone) to obtain a solution of the morpholine derivative free base in acetone, chloroform, acetonitrile, ethyl acetate, methanol, or tetrahydrofuran, dissolving acetic acid in acetone to obtain a solution of acetic acid in acetone, dropwisely adding the solution of acetic acid in acetone into the solution of the morpholine derivative free base in acetone, chloroform, acetonitrile, ethyl acetate, methanol, or tetrahydrofuran, stirring overnight at room temperature to precipitate a white solid, and filtering. Preferably, the molar ratio of the morpholine derivative free base to acetic acid is 1:1.1 to 1:3.1, preferably 1:1.4.

Compared with the prior art, the morpholine derivative acetate has one or more improved properties, e.g., it has a better crystalline state and greatly improved water solubility (150-300 mg/mL), but it is very hydroscopic, and it has good thermal stability under light condition.

In the fifth aspect, the present invention provides a morpholine derivative naphthalene disulfonate and a process for producing the same.

The morpholine derivative naphthalene disulfonate is a compound formed by the morpholine derivative and naphthalene disulfonic acid in a molar ratio of 1:1, and represented by the following structural formula:

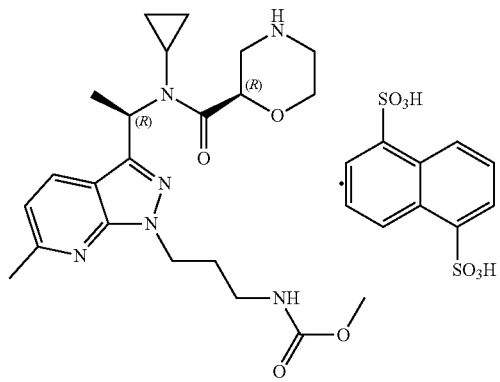

The morpholine derivative naphthalene disulfonate is amorphous.

Further, the morpholine derivative naphthalene disulfonate exhibits an X-ray powder diffraction (XRPD) pattern as shown in FIG. 31.

The method for preparing the morpholine derivative naphthalene disulfonate comprises the following steps: dissolving the morpholine derivative free base in ethyl acetate, dissolving naphthalene disulfonic acid in ethanol, dropwisely adding the solution of naphthalene disulfonic acid in ethanol into the solution of morpholine derivative free base in ethyl acetate, stirring at room temperature to give a white flocculent precipitate, and filtering. Preferably, the molar ratio of the morpholine derivative free base to naphthalene disulfonic acid is 1:1.1 to 1:3, preferably 1:1.4.

Compared with the prior art, the morpholine derivative naphthalene disulfonate has one or more improved properties, e.g., it has a better crystalline state and greatly improved water solubility (>500 mg/mL), but it is very hydroscopic, and it has good thermal stability under light condition.

The "stirring" mentioned in any of the above preparation methods of the present invention can be accomplished by conventional techniques such as magnetic stirring and mechanical stirring. The stirring speed may be 50 to 1800 rpm, preferably 300 to 900 rpm.

In the present invention, "room temperature" means 15-25° C.

In the present invention, "overnight" means 24 hours or more.

Further, the present invention provides a pharmaceutical composition comprising a therapeutically and/or prophylactically effective amount of one or more morpholine derivative salts of the present invention or crystal forms thereof, or the morpholine derivative salts or crystal forms thereof prepared by the method of the present invention, and at least one pharmaceutically acceptable excipient. Wherein, the morpholine derivative salts or the crystal forms thereof are selected from the group consisting of malate, tartrate, tartrate crystal form A, tartrate crystal form B, hydrochloride, acetate, naphthalene disulfonate of the morpholine derivative, in addition, the pharmaceutical composition may also include other pharmaceutically acceptable salt forms, crystal forms, or amorphous forms of the morpholine derivative.

Excipients in the pharmaceutical composition include sugars, cellulose and its derivatives, starch or modified starch, solid inorganic materials such as calcium phosphate, dicalcium phosphate, hydroxyapatite, calcium sulfate, calcium carbonate, semi-solid such as lipids or paraffins, binders such as microcrystalline cellulose, ethyl cellulose, hydroxymethyl cellulose, hydroxypropyl methyl cellulose, hydroxyethyl cellulose, glidants such as colloidal silica, light anhydrous silicic acid, crystalline cellulose, talc or magnesium stearate, disintegrants such as sodium starch glycolate, crospovidone, croscarmellose, sodium carboxymethyl cellulose, dry corn starch, lubricants such as stearic acid, magnesium stearate, sodium stearyl fumarate, polyethylene glycol.

The pharmaceutical composition may be either in solid or in liquid state, such as solid oral dosage forms, including tablets, granules, powders, pills and capsules; liquid oral dosage forms, including solutions, syrups, suspensions, dispersions and emulsions; injectable formulations, including solutions, dispersions and lyophilisates. The formulation may be suitable for rapid release, delayed release or modified release of the active ingredient. It may be a conventional, dispersible, chewable, oral soluble or rapidly melting formulation. The administration route includes oral administration, intravenous subcutaneous injection, administration by injecting into tissue, transdermal administration, rectal administration, intranasal administration, and the like.

The pharmaceutical composition may be prepared by using methods known to those skilled in the art. When preparing the pharmaceutical composition, the morpholine derivative salt or crystal form thereof of the present invention is mixed with one or more pharmaceutically acceptable carriers, optionally mixed with pharmaceutically acceptable other crystal forms, other amorphous forms or salt forms of the morpholine derivative, optionally mixed with one or more other active ingredients. Solid formulations may be prepared by processes such as direct mixing, granulation, and the like.

Further, the present invention provides a use of the aforementioned morpholine derivative salt or crystal form thereof according to the present invention as a renin inhibitor, and a use thereof in the preparation of a drug for the treatment and/or prevention of diseases such as hypertension, cardiac insufficiency, diabetic nephropathy, etc.

DESCRIPTION OF THE EMBODIMENTS

Figure 1:
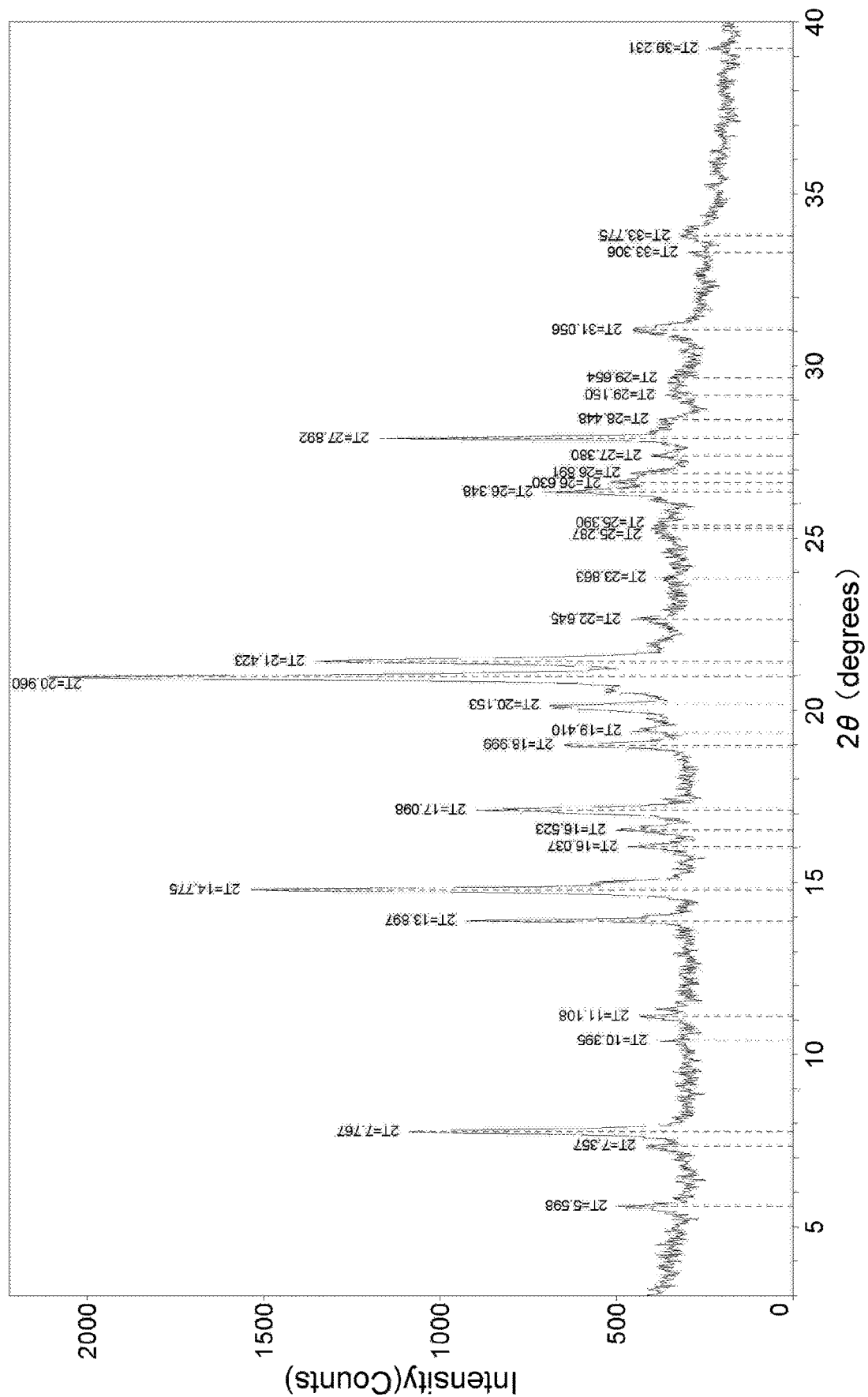
FIG. 1 is an XRPD pattern of the morpholine derivative malate.

The present invention will be further described with reference to the following examples, and the preparation methods and applications of the salts and crystal forms of the present invention will be described in detail in the examples. It will be apparent to those skilled in the art that various changes made to materials and methods may be implemented without departing from the scope of the present invention.

Test instruments and methods:
The instrument used for X-ray powder diffraction (XPRD) was Bruker D8 Advance diffractometer equipped with a θ-2θ goniometer, a Mo Monochromator and a Lynx-eye detector. The test was carried out using K X-ray with a wavelength of L54 nm at a copper target under the operation condition of 40 kV and 40 mA. The instrument was calibrated for the peak position with the standard sample that comes with the instrument before use. The software for collecting data was Diffrac Plus XRD Commander and the analysis software was MDI Jade 5.0. The sample was tested at room temperature and the sample to be tested was placed on an organic slide. The detailed detection conditions were as follows: angle range: 3-4°2θ; step length: 0.02°2θ; speed: 0.2 s/step. Samples were not ground prior to testing unless otherwise specified.

Polarized light microscope (PLM) image was obtained from an XP-500E polarized light microscope (Shanghai Changfang Optical Instrument Co., Ltd.). A small amount of powder sample was placed on a glass slide, a small amount of mineral oil was dropwisely added to better disperse the powder sample, and a cover glass was then placed thereon, and then the sample was placed on the stage of XP-500E polarized light microscope (Shanghai Changfang Optical Instrument Co., Ltd.). The morphology of the sample was observed and photographed with an appropriate magnification.

Differential Scanning Calorimetry (DSC) data was taken from a TA Instruments Q200 MDSC, instrument control software was Thermal Advantage, and analysis software was Universal Analysis. Generally, 1 to 10 mg of sample was placed in an aluminum crucible with a punched lid (unless otherwise specified), and the sample was heated from room temperature to 200° C. or 300° C. at a rate of 10° C./min under the protection of 50 mL/min dry $N_2$, meanwhile, the TA software recorded the heat change of the sample during the heating process. In the present application, the melting point is reported as the starting temperature.

Thermogravimetric Analysis (TGA) data was taken from a TA Instruments Q500 TGA, instrument control software was Thermal Advantage, and analysis software was Universal Analysis. Generally, 5 to 15 mg of the sample was placed in a platinum crucible, and, in a segmented and high resolution detection mode, the sample was heated from room temperature to 300° C. at a rate of 10° C./min under the protection of 50 mL/min dry $N_2$, meanwhile, the TA software recorded the weight change of the sample during the heating process.

Dynamic Vapor Sorption Analysis (DVS) data was taken from a TA Instruments Q5000 TGA, instrument control software was Thermal Advantage, and analysis software was Universal Analysis. Generally, 1 to 10 mg of the sample was placed in a platinum crucible, the TA software generally recorded the weight change of the sample as the relative humidity changed from 0% to 80% to 0%. According to the specific conditions of the sample, different adsorption and desorption steps might also be applied to the sample.

The morpholine derivative free base, the starting material of the present invention, was prepared according to the method disclosed in the document CN 103562191 (WO 2012124775). In the following examples, the morpholine derivative free base is referred as the free base.

Example 1

Preparation of the Morpholine Derivative Malate 10.64 mg (0.024 mmol, 1 eq) of the free base was dissolved in 0.6 ml of acetone, 3.63 mg (0.027 mmol, 1.1 eq) of L-malic acid was dissolved in 0.04 ml of ethanol, and then the formulated ethanol solution was added dropwisely to the acetone solution. The mixture was stirred overnight at room temperature to precipitate a white solid that was filtered and characterized.

The morpholine derivative malate exhibits an X-ray powder diffraction (XRPD) pattern as shown in FIG. 1.

Figure 2:
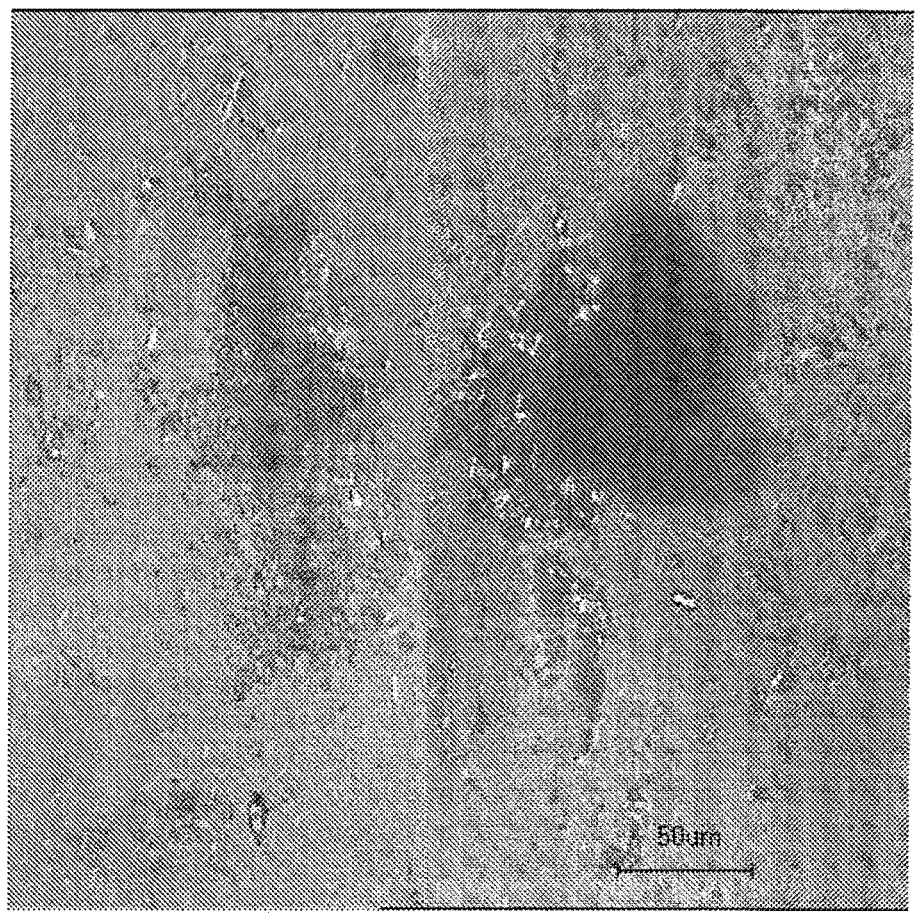
FIG. 2 is a PLM image of the morpholine derivative malate.

The morpholine derivative malate exhibits a Polarized Light Microscope (PLM) image as shown in FIG. 2.

Figure 3:
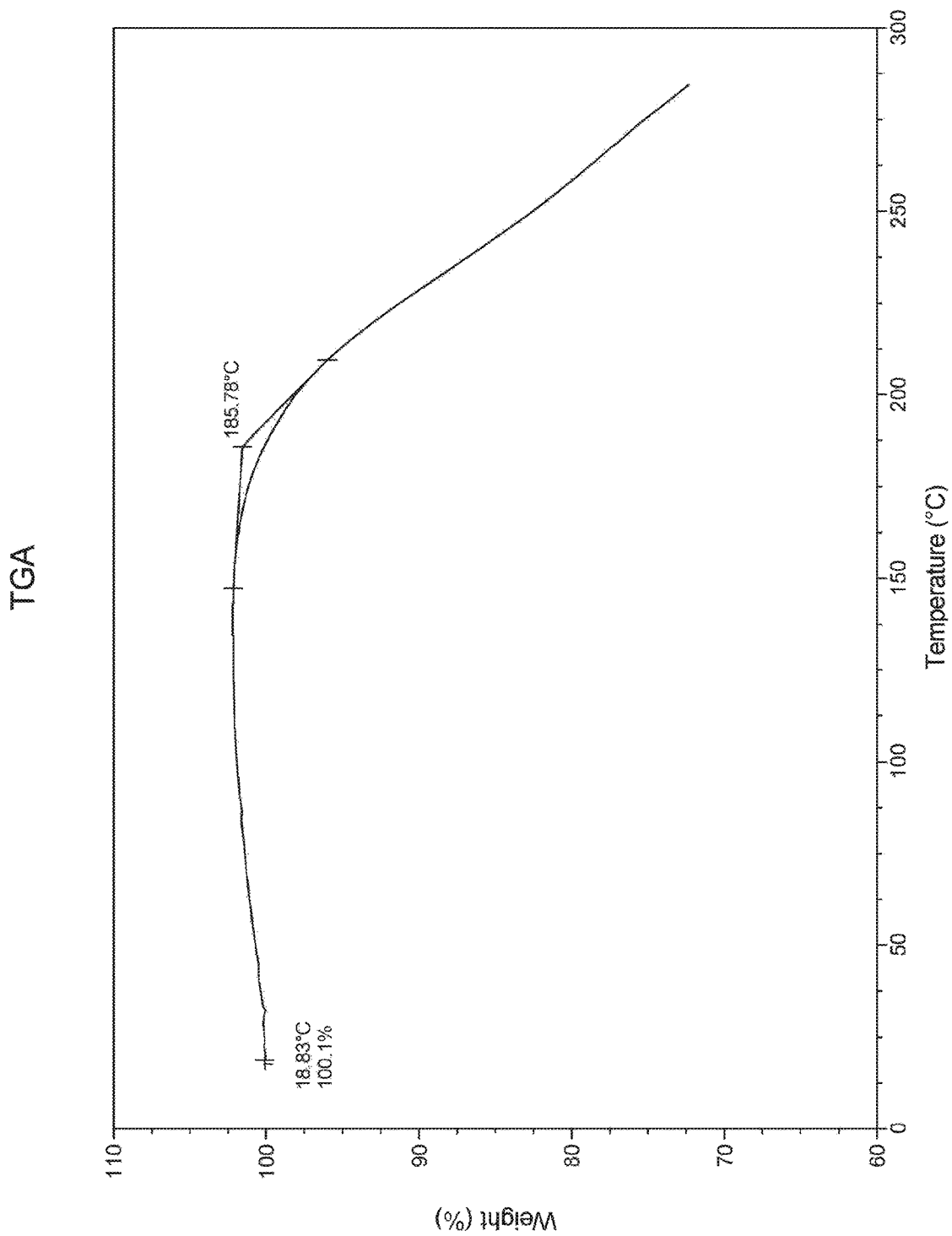
FIG. 3 is a TGA plot of the morpholine derivative malate.

The morpholine derivative malate exhibits a Thermogravimetric Analysis (TGA) plot as shown in FIG. 3, and the TGA plot shows that the morpholine derivative malate is decomposed at about 185.8° C., and the sample loses no weight before decomposition.

Figure 4:
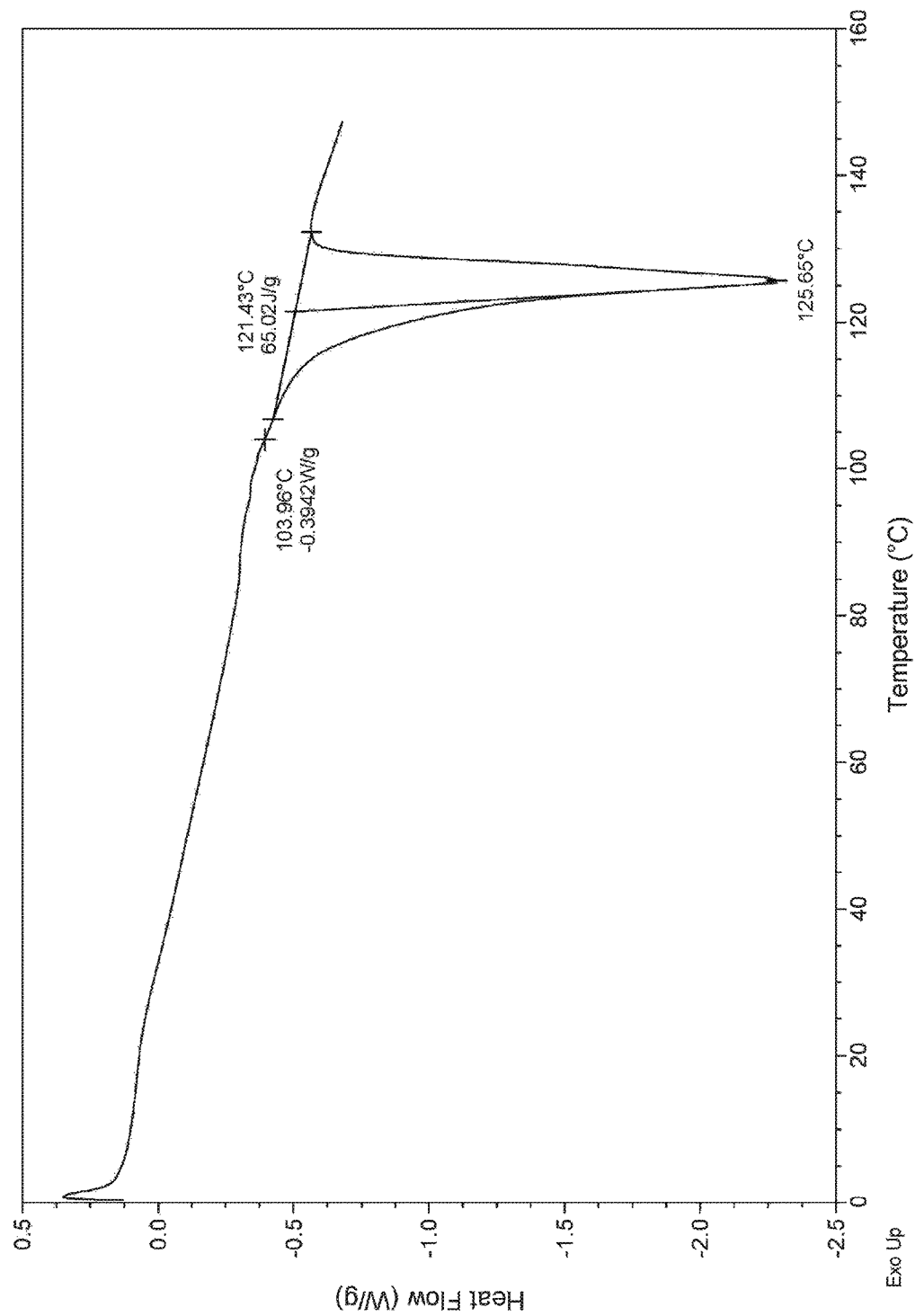
FIG. 4 is a DSC plot of the morpholine derivative malate.

The morpholine derivative malate exhibits a Differential Scanning Calorimetry (DSC) plot as shown in FIG. 4, and the DSC plot shows an endothermic peak (95 J/g) at about 121° C.

Figure 5:
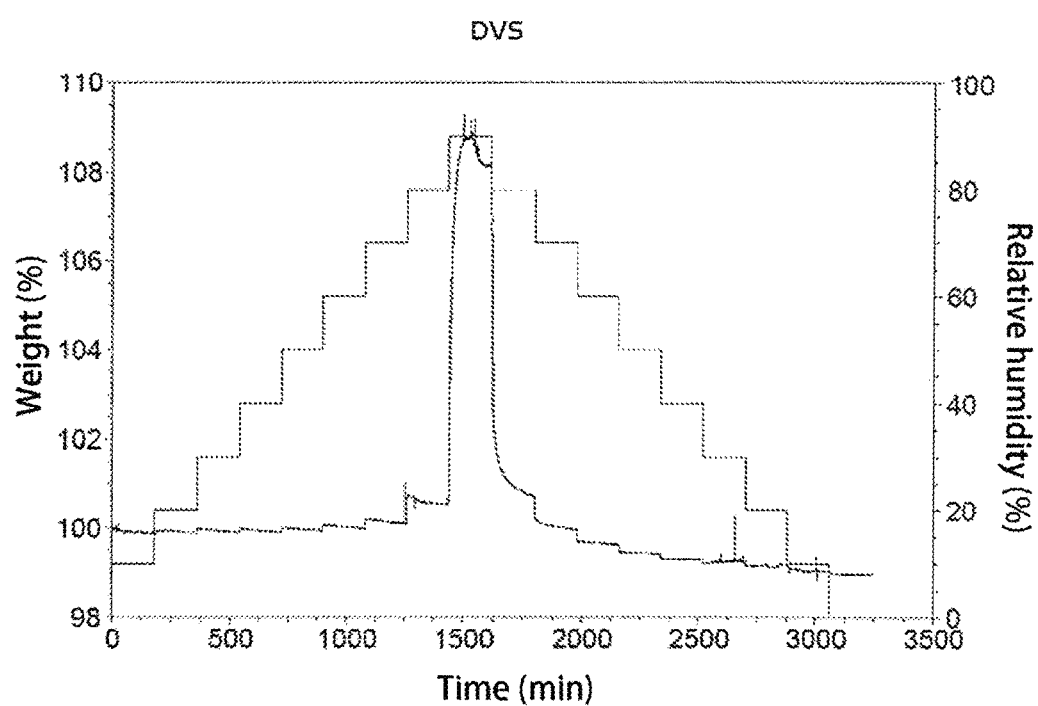
FIG. 5 is a DVS plot of the morpholine derivative malate.

The morpholine derivative malate exhibits a Dynamic Vapor Sorption Analysis (DVS) plot as shown in FIG. 5, and the DVS plot shows that the morpholine derivative malate has a weight change of about 1.2% in a range of 20%-80% humidity.

Example 2

Preparation of the Morpholine Derivative Tartrate Crystal Form B 42.72 mg (0.096 mmol, 1 eq) of the free base was dissolved in 1.0 ml of acetone, 14.86 mg (0.099 mmol, 1.03 eq) of L-tartaric acid was dissolved in 0.048 ml of water, and then the formulated aqueous solution of L-tartaric acid was added dropwisely to the solution of the free base in acetone. The mixture was stirred overnight at room temperature to precipitate a white solid that was filtered and characterized.

Figure 6:
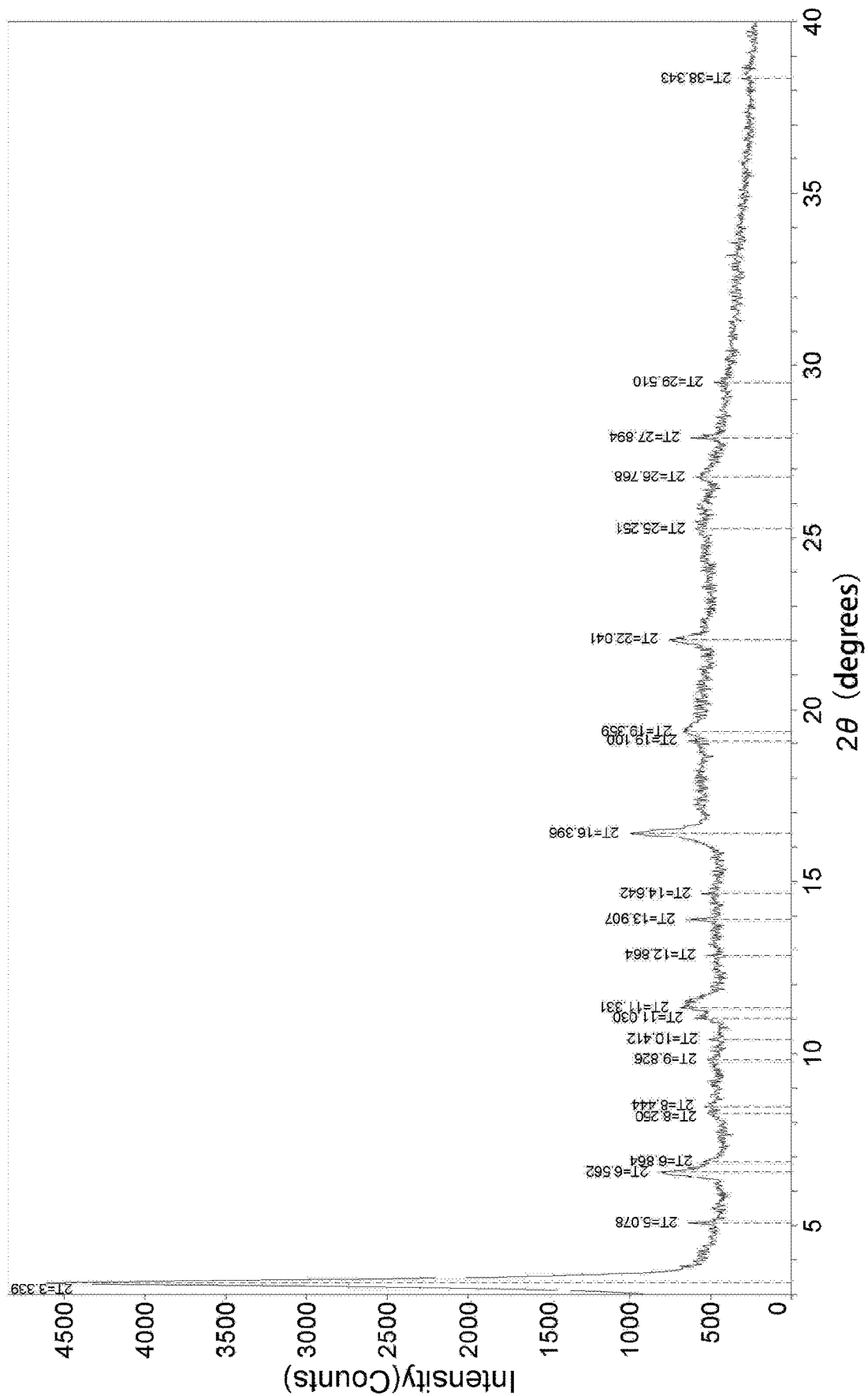
FIG. 6 is an XRPD pattern of the morpholin derivative tartrate crystal form B.

The morpholine derivative tartrate crystal form B exhibits an XRPD pattern as shown in FIG. 6.

Figure 7:
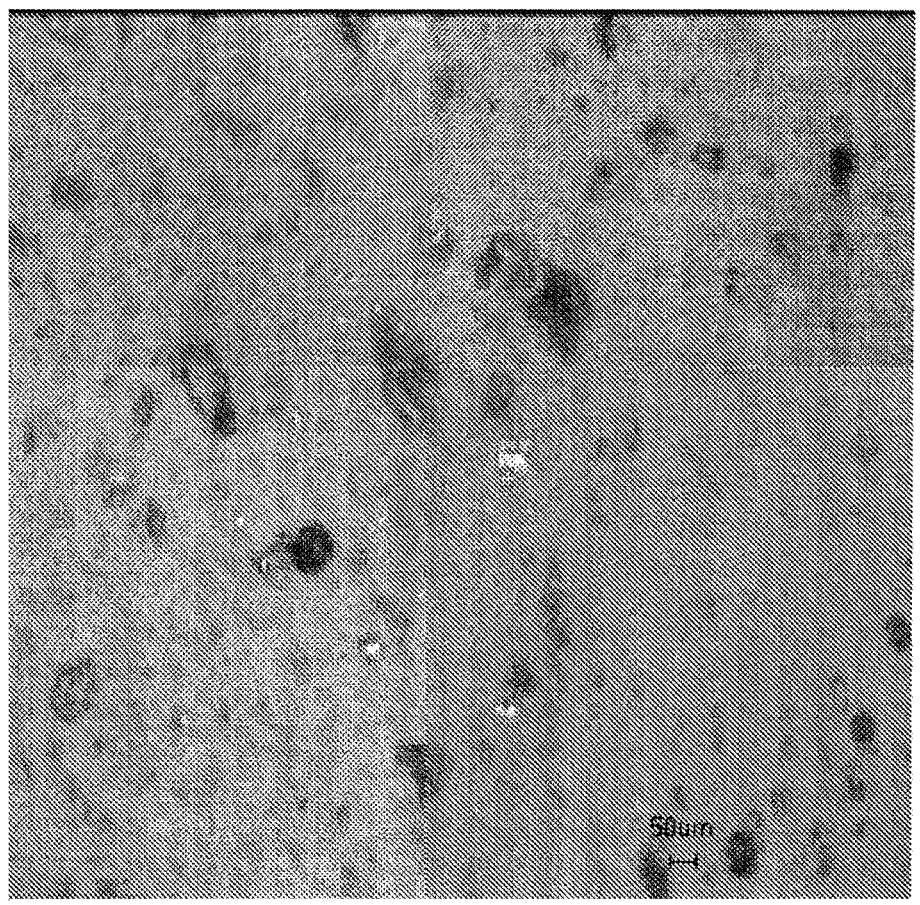
FIG. 7 is a PLM image of the morpholin derivative tartrate crystal form B.

The morpholine derivative tartrate crystal form B exhibits a PLM image as shown in FIG. 7.

Figure 8:
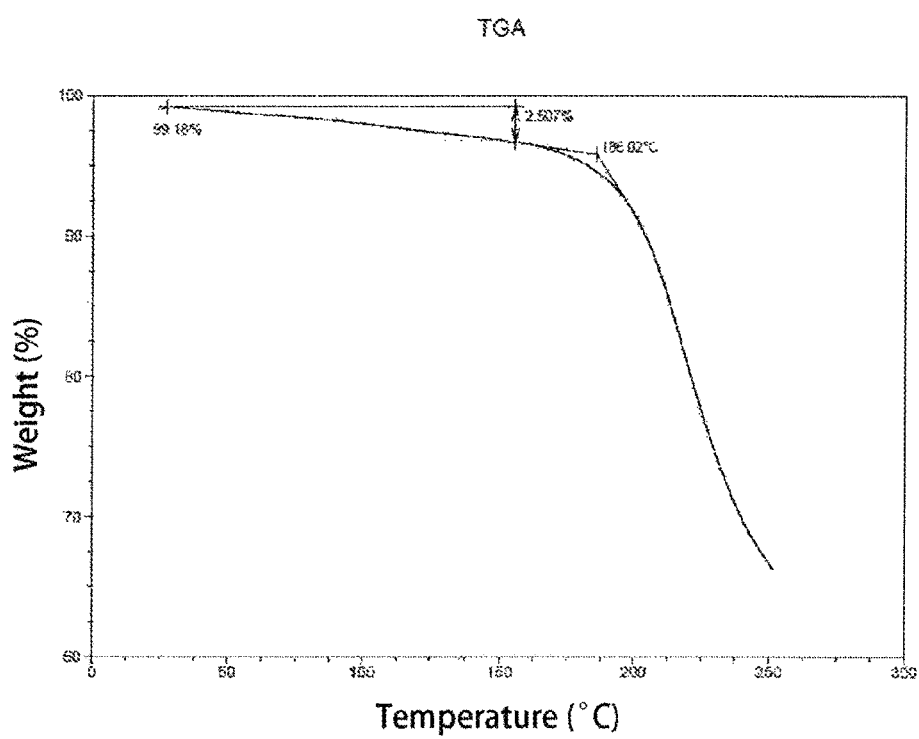
FIG. 8 is a TGA plot of the morpholin derivative tartrate crystal form B.

The morpholine derivative tartrate crystal form B exhibits a TGA plot as shown in FIG. 8, the TGA plot shows that the morpholine derivative tartrate crystal form B is decomposed at about 186.0° C., and 2.5% of the weight is slowly lost before decomposition (the weight begins to lose at about 150° C.).

Figure 9:
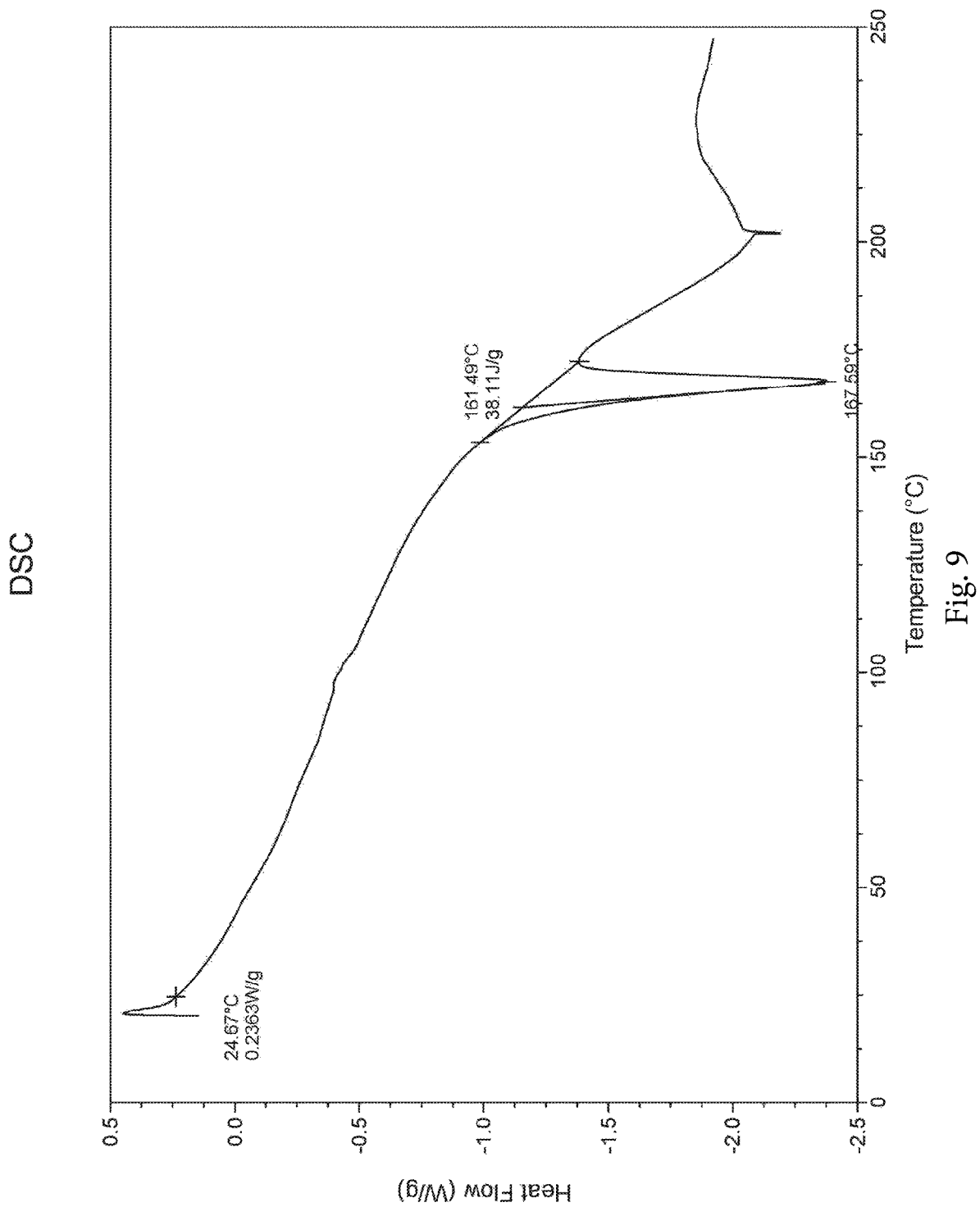
FIG. 9 is a DSC plot of the morpholin derivative tartrate crystal form B.

The morpholine derivative tartrate crystal form B exhibits a DSC plot as shown in FIG. 9, and the DSC plot shows that the morpholine derivative tartrate crystal form B has an endothermic peak (38 J/g) at about 161.5° C.

Figure 10:
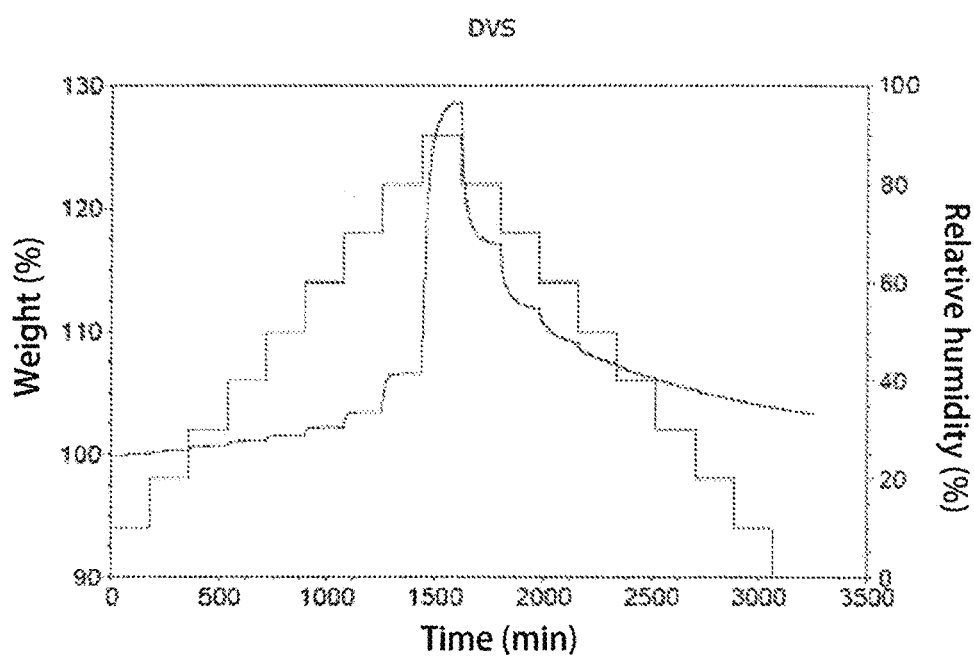
FIG. 10 is a DVS plot of the morpholin derivative tartrate crystal form B.

The morpholine derivative tartrate crystal form B exhibits a DVS plot as shown in FIG. 10, and the DVS plot shows that the weight change is about 7% in a range of 20%-80% humidity, it is relatively hydroscopic, and may become a hydrate.

Example 3

Preparation of the Morpholine Derivative Tartrate Dihydrate 10 mg of the morpholine derivative tartarate crystal form B prepared in Example 2 was added with a 50 ml of a mixed solvent of acetone and water in a volume ratio of 30:1. The mixture was stirred at room temperature for 2 days, then filtered and characterized.

Figure 11:
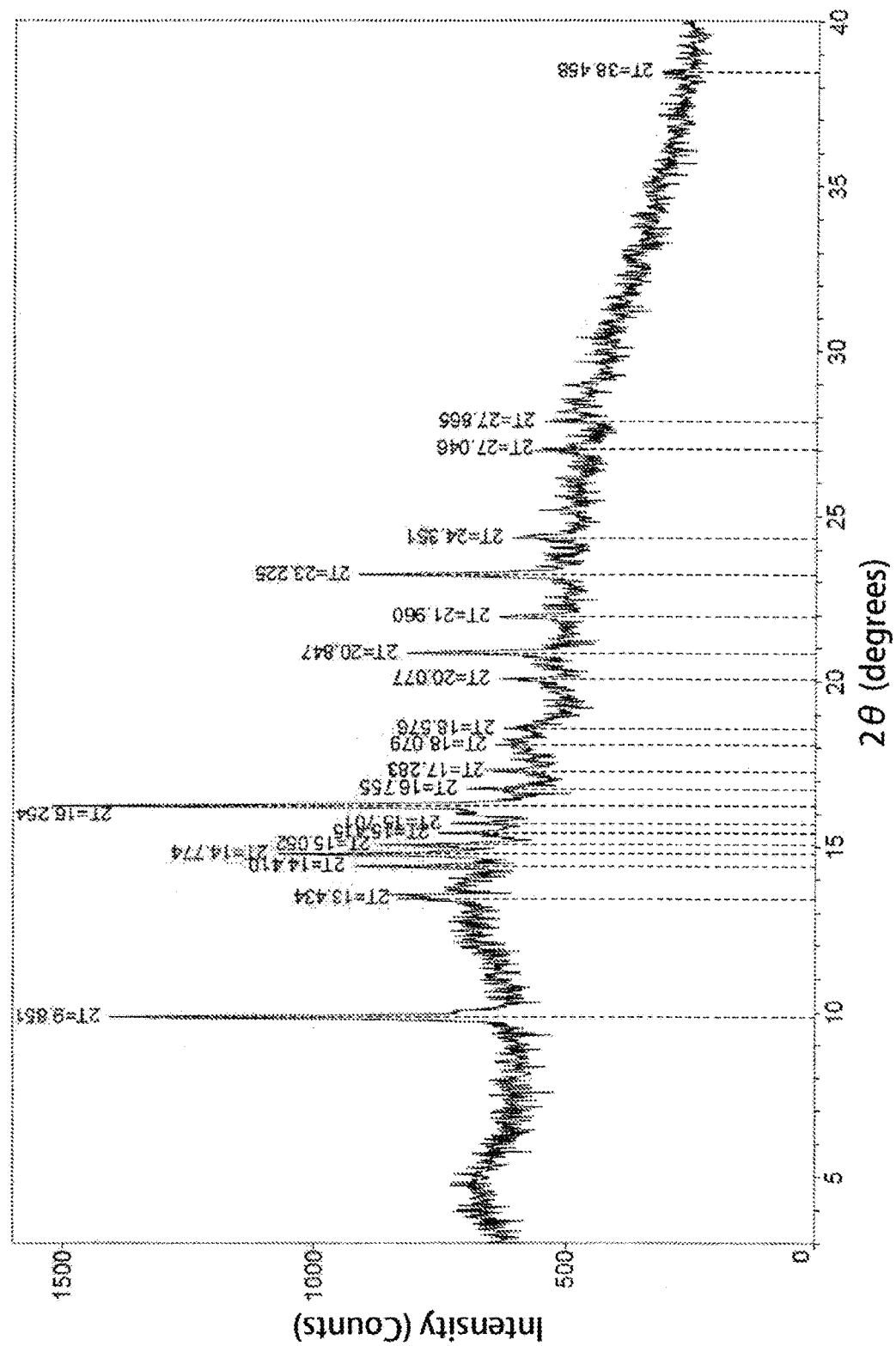
FIG. 11 is an XRPD pattern of the morpholine derivative tartrate dihydrate.

The morpholine derivative tartrate dihydrate exhibits an XRPD pattern as shown in FIG. 11.

Figure 12:
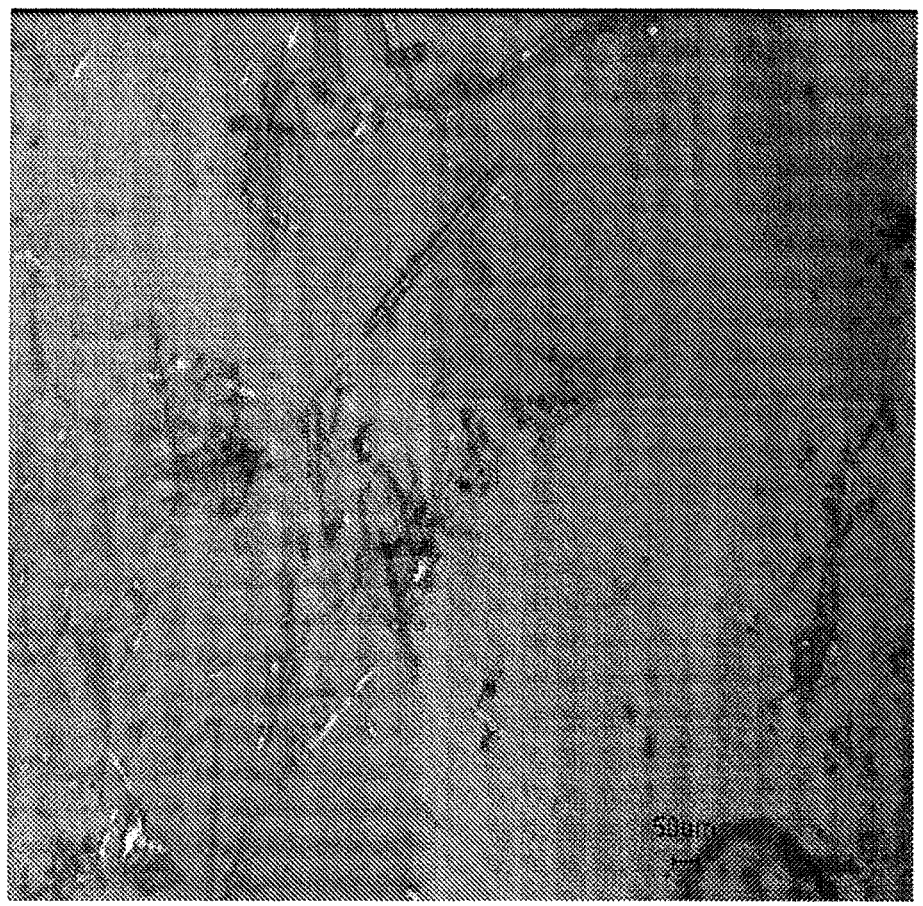
FIG. 12 is a PLM image of the morpholine derivative tartrate dihydrate.

The morpholine derivative tartrate dihydrate exhibits a PLM image as shown in FIG. 12.

Figure 13:
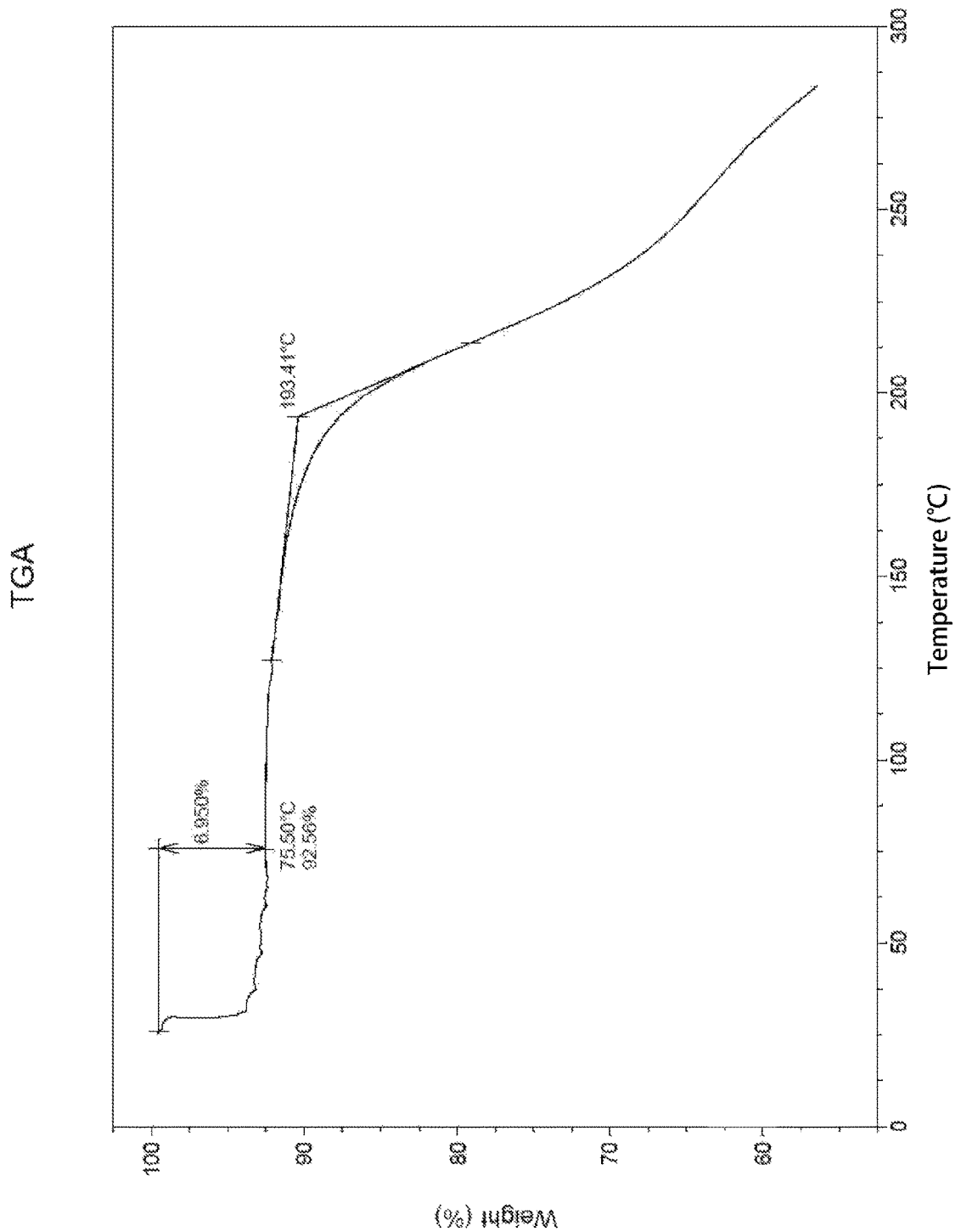
FIG. 13 is a TGA plot of the morpholine derivative tartrate dihydrate.

The morpholine derivative tartrate dihydrate exhibits a TGA plot as shown in FIG. 13, the TGA plot shows that the morpholine derivative tartrate dihydrate is decomposed at about 189.6° C., and 6.95% of the weight is gradiently lost before decomposition.

Figure 14:
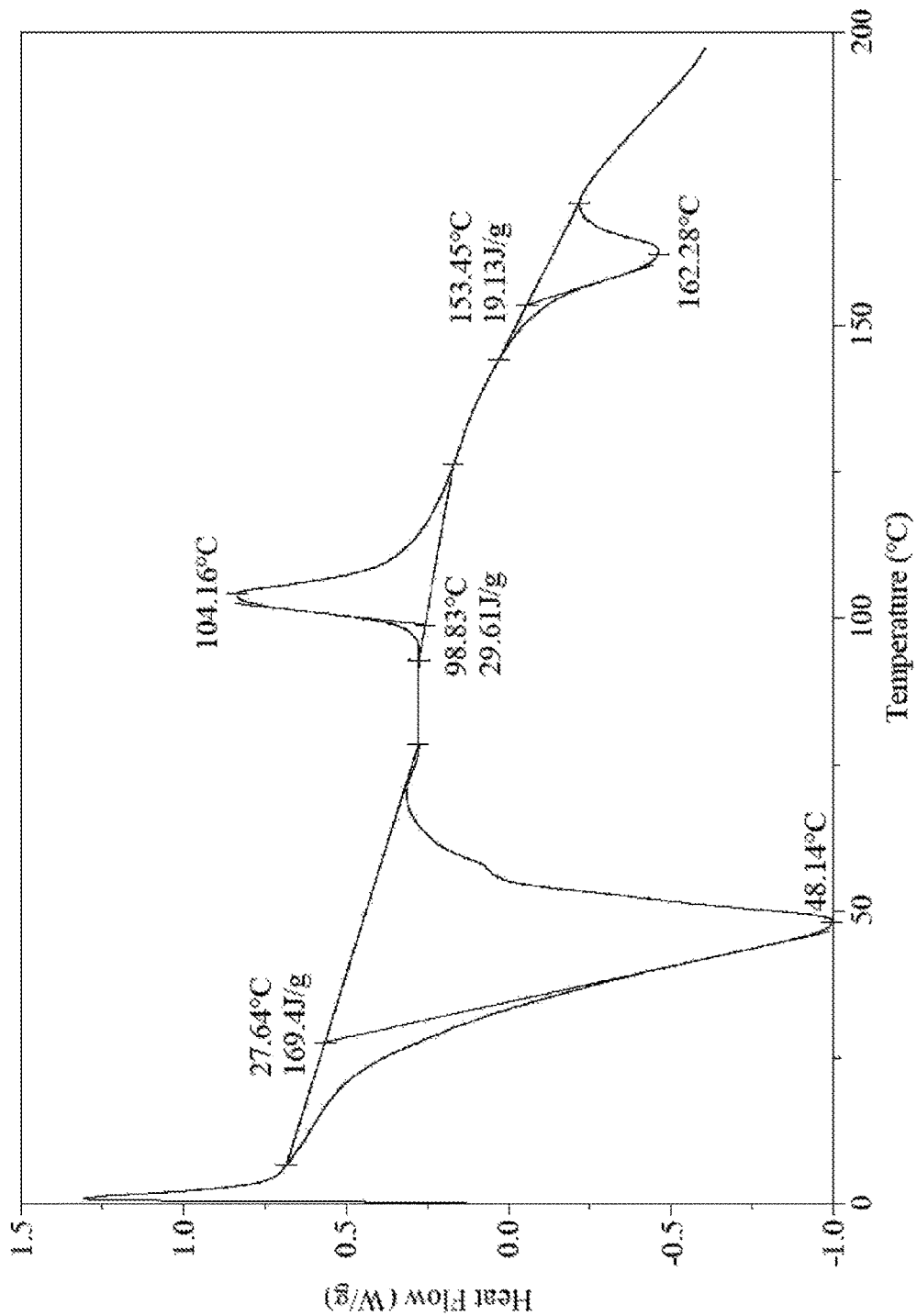
FIG. 14 is a DSC plot of the morpholine derivative tartrate dihydrate.

The morpholine derivative tartrate dihydrate exhibits a DSC plot as shown in FIG. 14, and the DSC plot shows that the morpholine derivative tartrate dihydrate has an endothermic peak (112 J/g) at about 29.5° C., an exothermic peak (27 J/g) at about 99° C., and an endothermic peak (19 J/g) at about 154° C.

Figure 15:
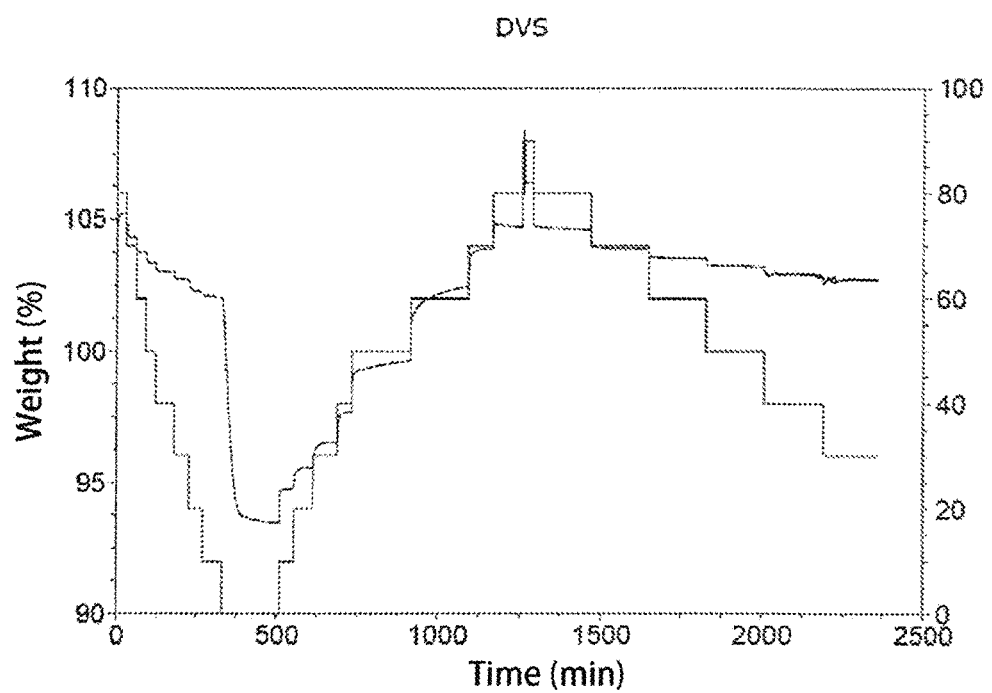
FIG. 15 is a DVS plot of the morpholine derivative tartrate dihydrate.

The morpholine derivative tartrate dihydrate exhibits a DVS plot as shown in FIG. 15, and the DVS plot shows that the weight change is about 11.06% in a range of 0%-80% humidity, and it is relatively hydroscopic.

Example 4

Preparation of the Morpholine Derivative Tartrate Crystal Form A (Tetrahydrate)

1.0 g of the free base (2.25 mmol, 1 eq) was dissolved in acetone and completely solubilized by sonication. 0.74 g of L-tartaric acid (4.93 mmol, 2.2 eq 20:1) was taken. The acid solution was slowly added dropwisely to the base solution, and the mixture was stirred at room temperature for not less than 48 hours, and 1.01 g of a tartrate hydrate solid was obtained by filtration.

Figure 16:
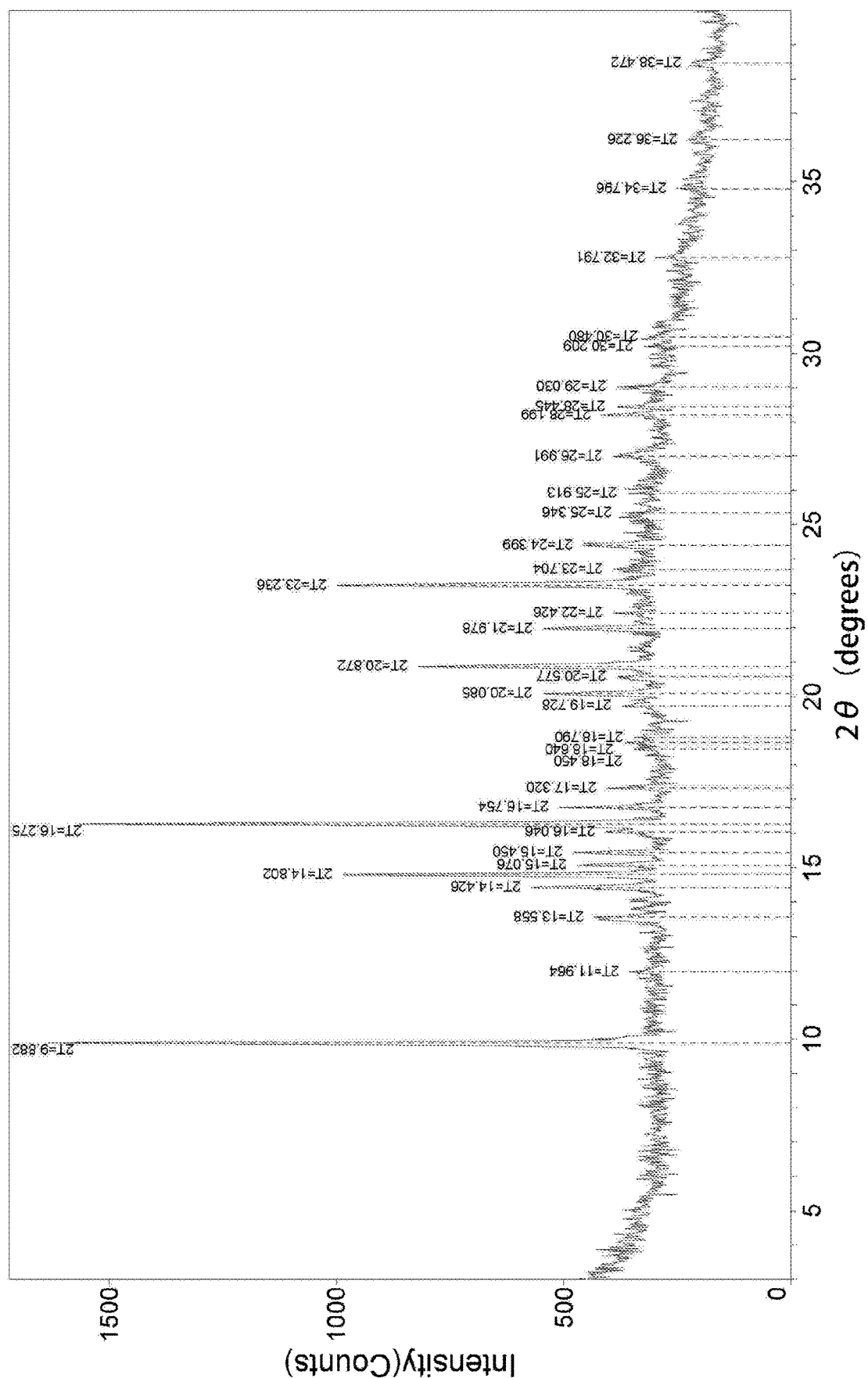
FIG. 16 is an XRPD pattern of the morpholine derivative tartrate crystal form A.

The morpholine derivative tartrate crystal form A exhibits an X-ray Powder Diffraction (XRPD) pattern as shown in FIG. 16.

Figure 17:
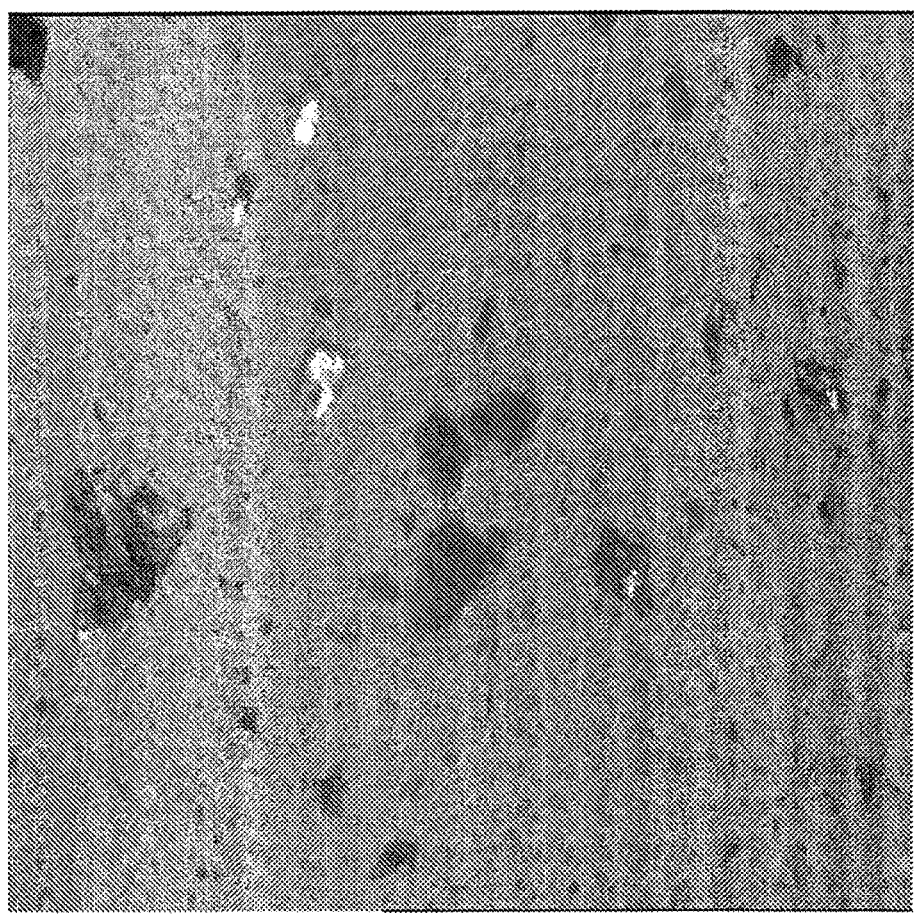
FIG. 17 is a PLM image of the morpholine derivative tartrate crystal form A.

The morpholine derivative tartrate crystal form A exhibits a Polarized Light Microscopy (PLM) image as shown in FIG. 17.

Figure 18:
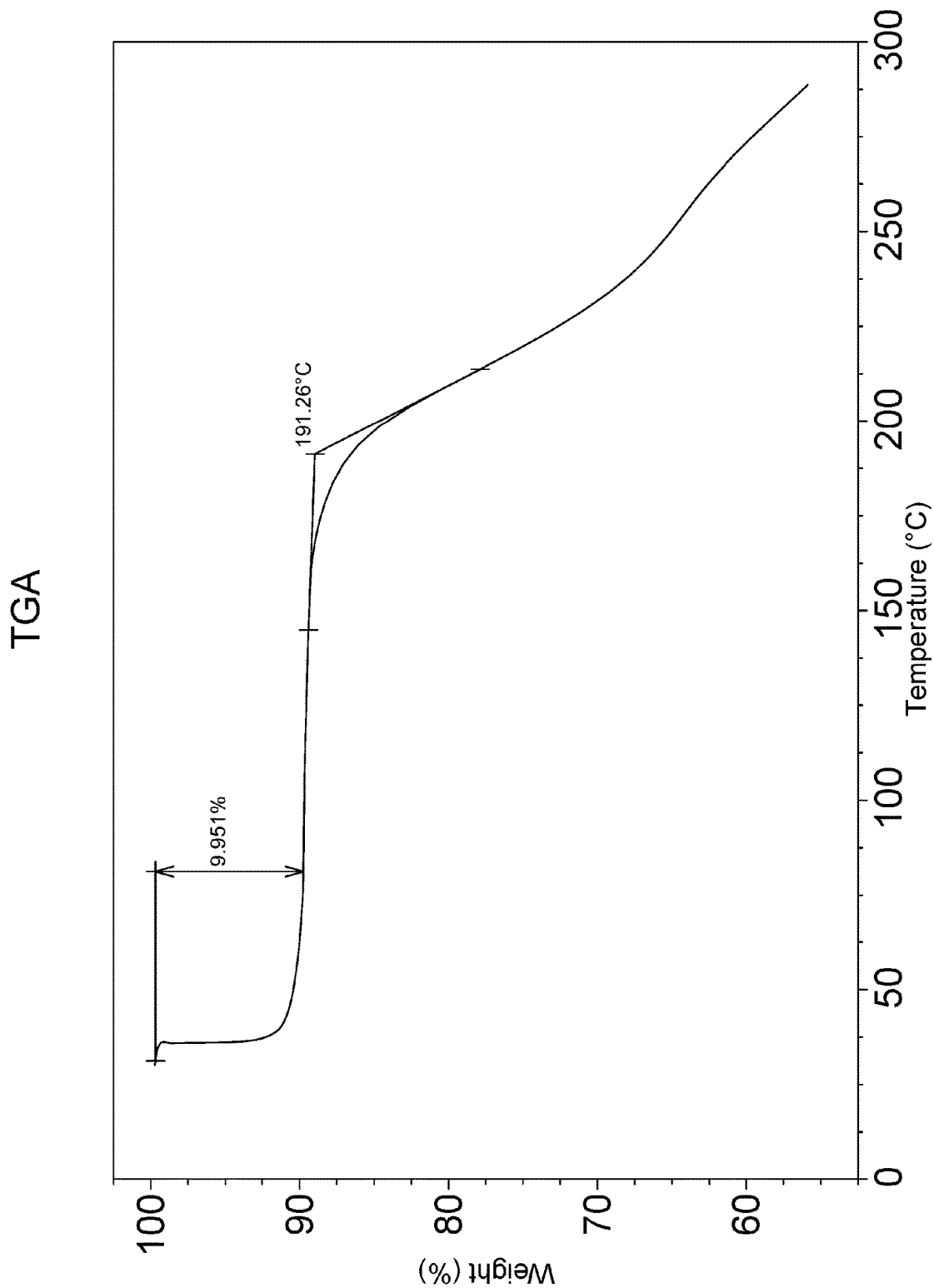
FIG. 18 is a TGA plot of the morpholine derivative tartrate crystal form A.

The morpholine derivative tartrate crystal form A exhibits a Thermogravimetric Analysis (TGA) plot as shown in FIG. 18 and the TGA plot shows that the morpholine derivative tartrate tetrahydrate loses 10.0-10.4% of the weight.

Figure 19:
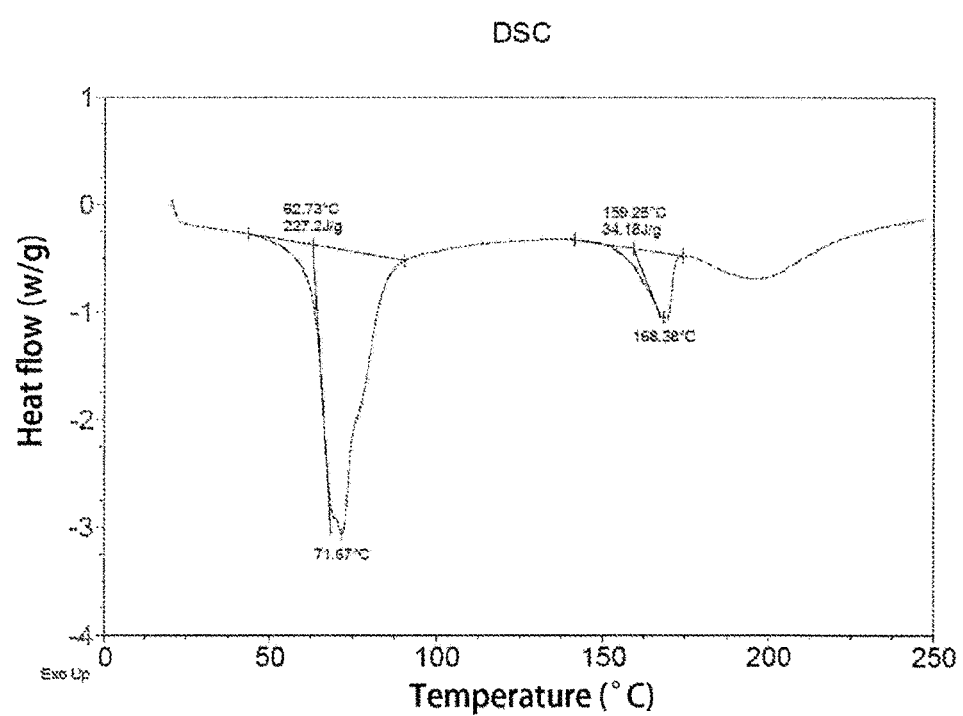
FIG. 19 is a DSC plot of the morpholine derivative tartrate crystal form A.

The morpholine derivative tartrate crystal form A exhibits a Differential Scanning Calorimetry (DSC) plot as shown in FIG. 19, and the DSC plot shows that the morpholine derivative tartrate crystal form A has an endothermic peak at 62.7° C., a melting endothermic peak at 159.3° C., and decomposes at 191° C. or higher.

Figure 20:
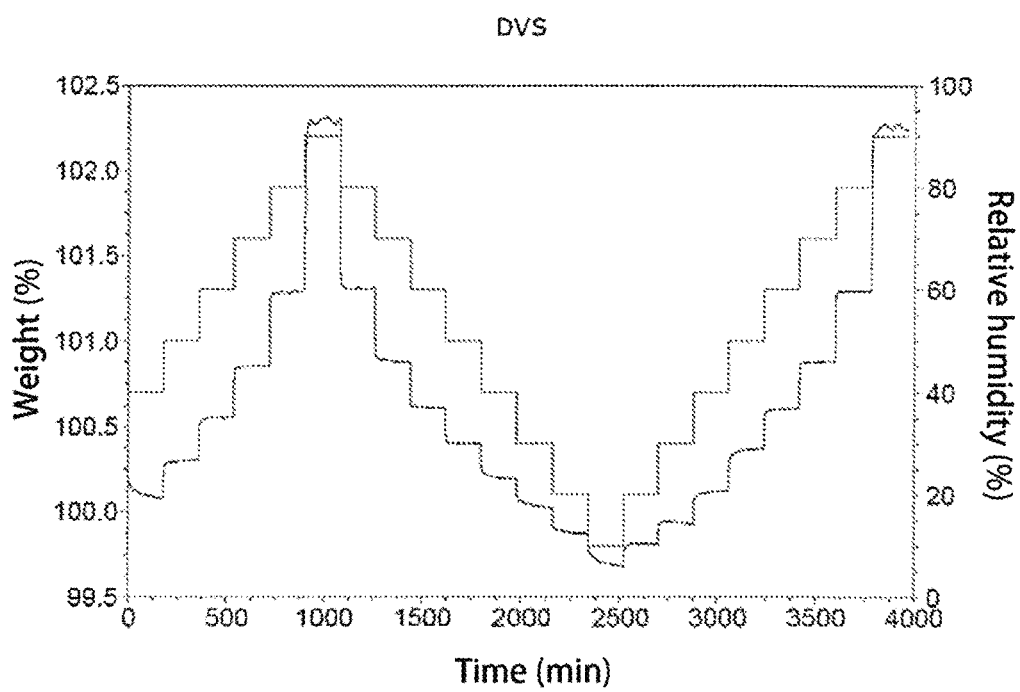
FIG. 20 is a DVS plot of the morpholine derivative tartrate crystal form A.

The morpholine derivative tartrate crystal form A exhibits a Dynamic Vapor Sorption Analysis (DVS) plot as shown in FIG. 20, and the DVS plot shows that the weight change of the morpholine derivative tartrate crystal form A is about 1.5% in a range of 20%-80% humidity, and it is hardly hydroscopic.

Example 5

Preparation of the Morpholine Derivative Hydrochloride 1.5 g of the free base (3.38 mmol, 1 eq) was dissolved in 50 mL of acetone and completely solubilized by sonication, and 1.1 g of 36.5% of aqueous solution of hydrochloric acid (10.8 mmol, 3.3 eq) was taken. Then the acid solution was slowly added dropwisely to the base solution, and the mixture was stirred overnight at room temperature. A hydrochloride solid was obtained by filtration.

Figure 21:
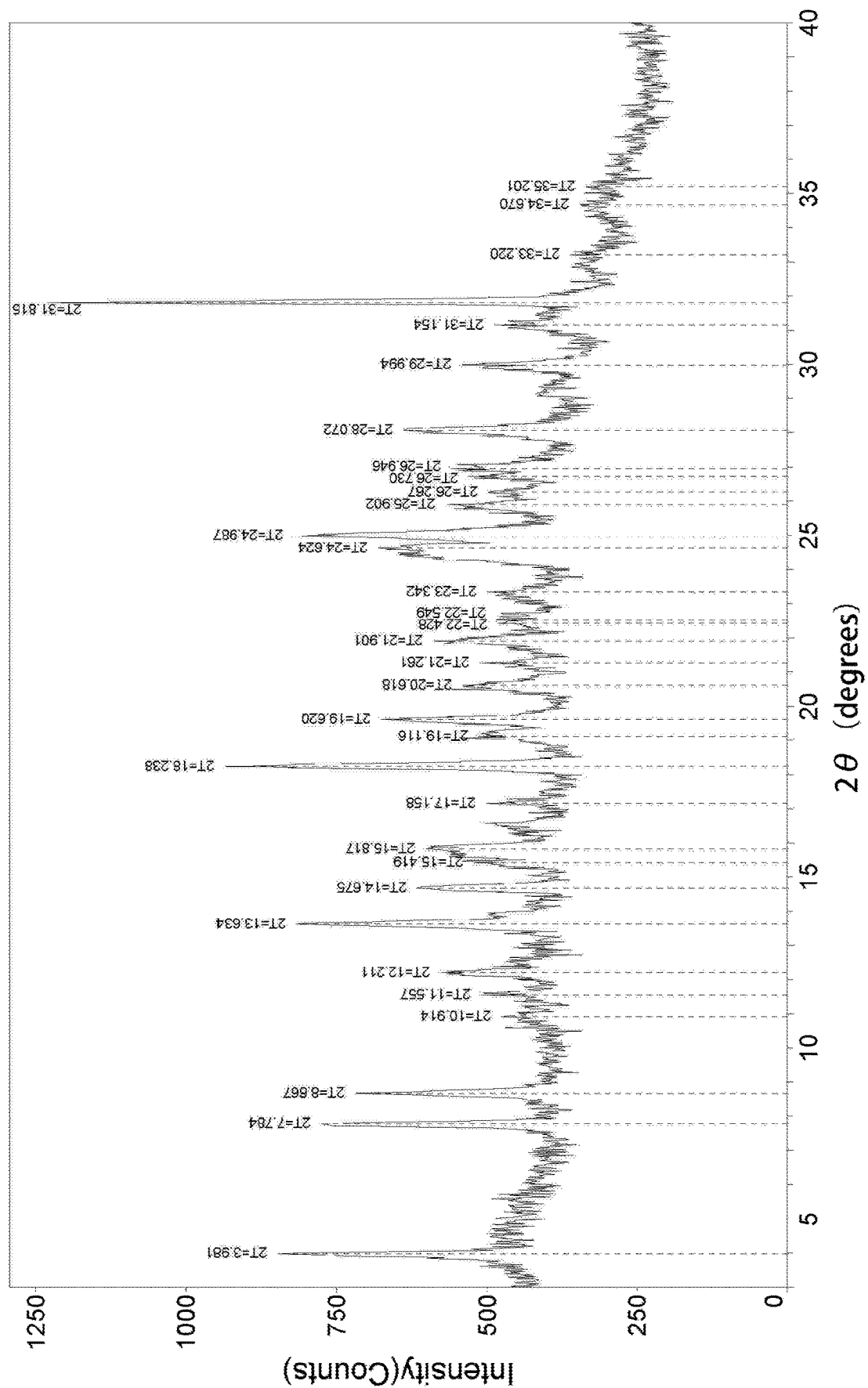
FIG. 21 is an XRPD pattern of the morpholine derivative hydrochloride.

The morpholine derivative hydrochloride exhibits an X-ray Powder Diffraction (XRPD) pattern as shown in FIG. 21.

Figure 22:
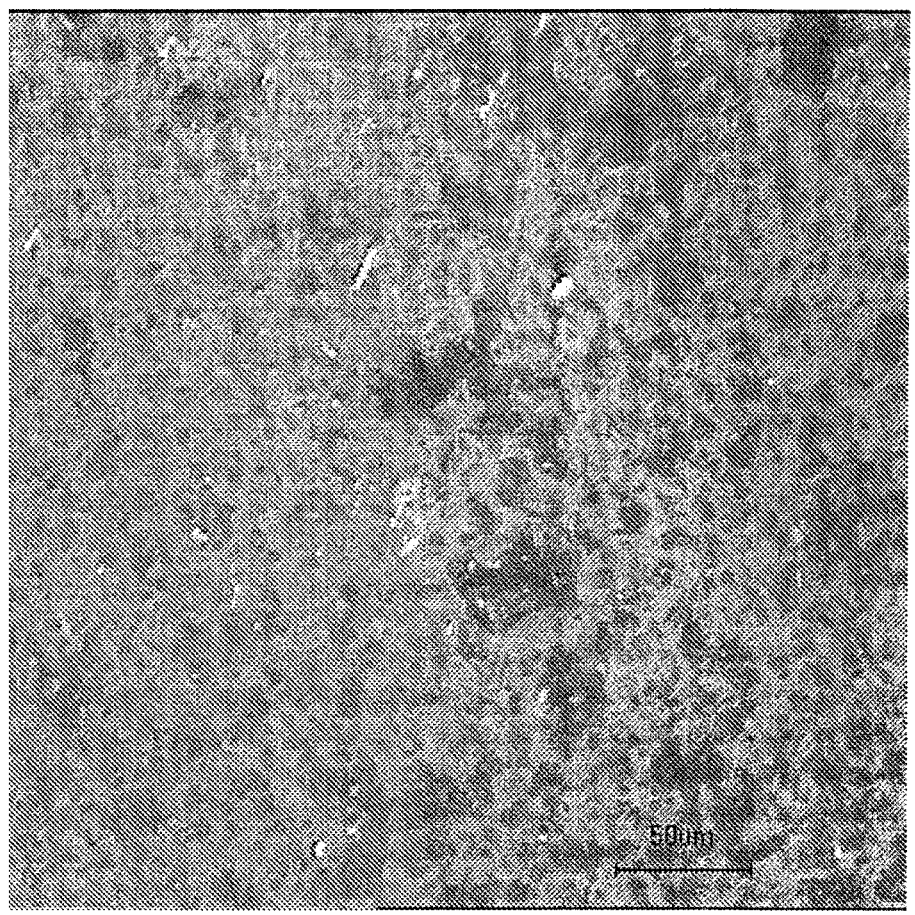
FIG. 22 is a PLM image of the morpholine derivative hydrochloride.

The morpholine derivative hydrochloride exhibits a Polarized Light Microscopy (PLM) image as shown in FIG. 22.

Figure 23:
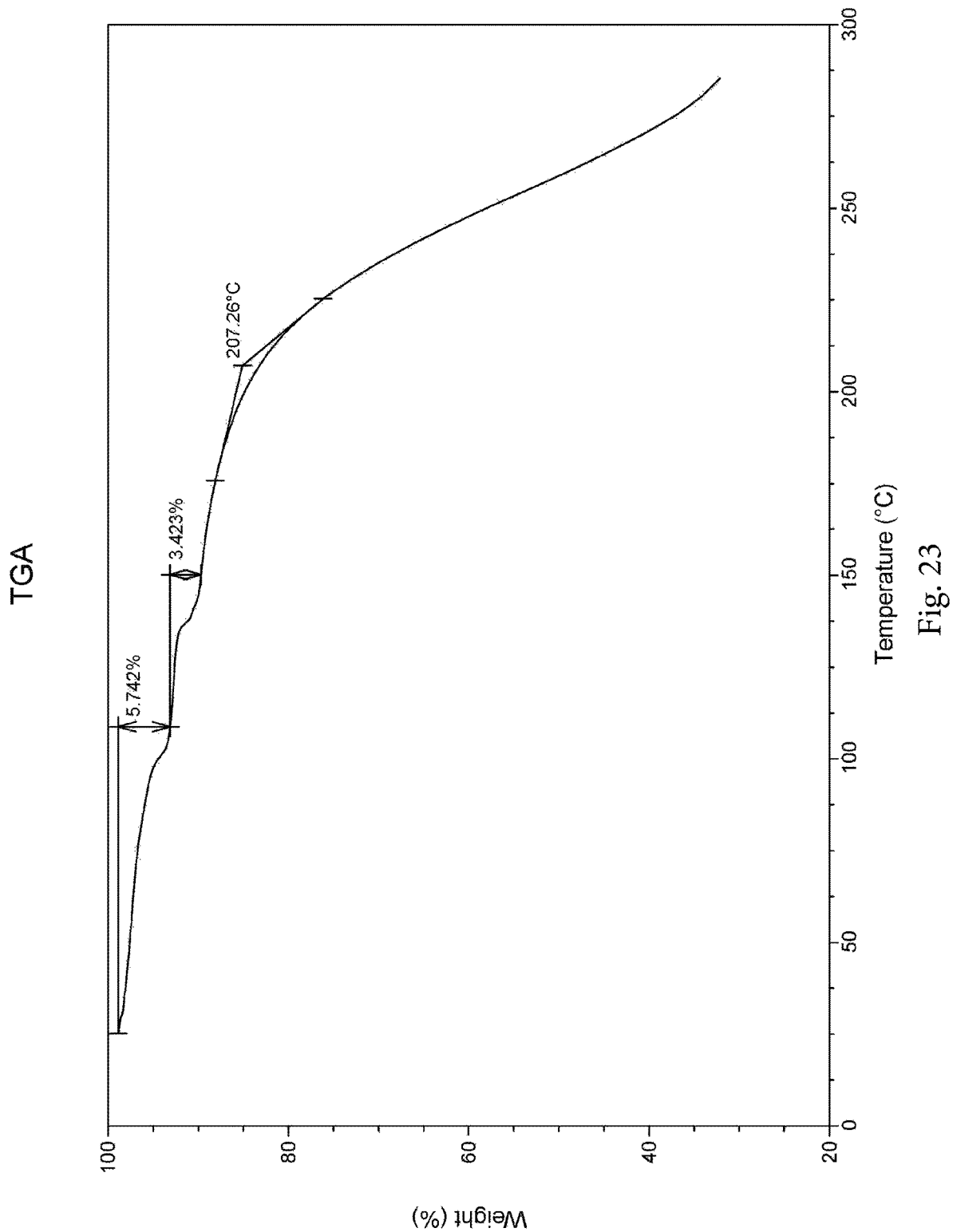
FIG. 23 is a TGA plot of the morpholine derivative hydrochloride.

The morpholine derivative hydrochloride exhibits a Thermogravimetric Analysis (TGA) plot as shown in FIG. 23, the TGA plot shows that the morpholine derivative hydrochloride continues to lose weight during the heating process, the decomposition temperature is 207° C. and there are two stages of weight loss before decomposition, and the total weight loss is about 9.1%.

Figure 24:
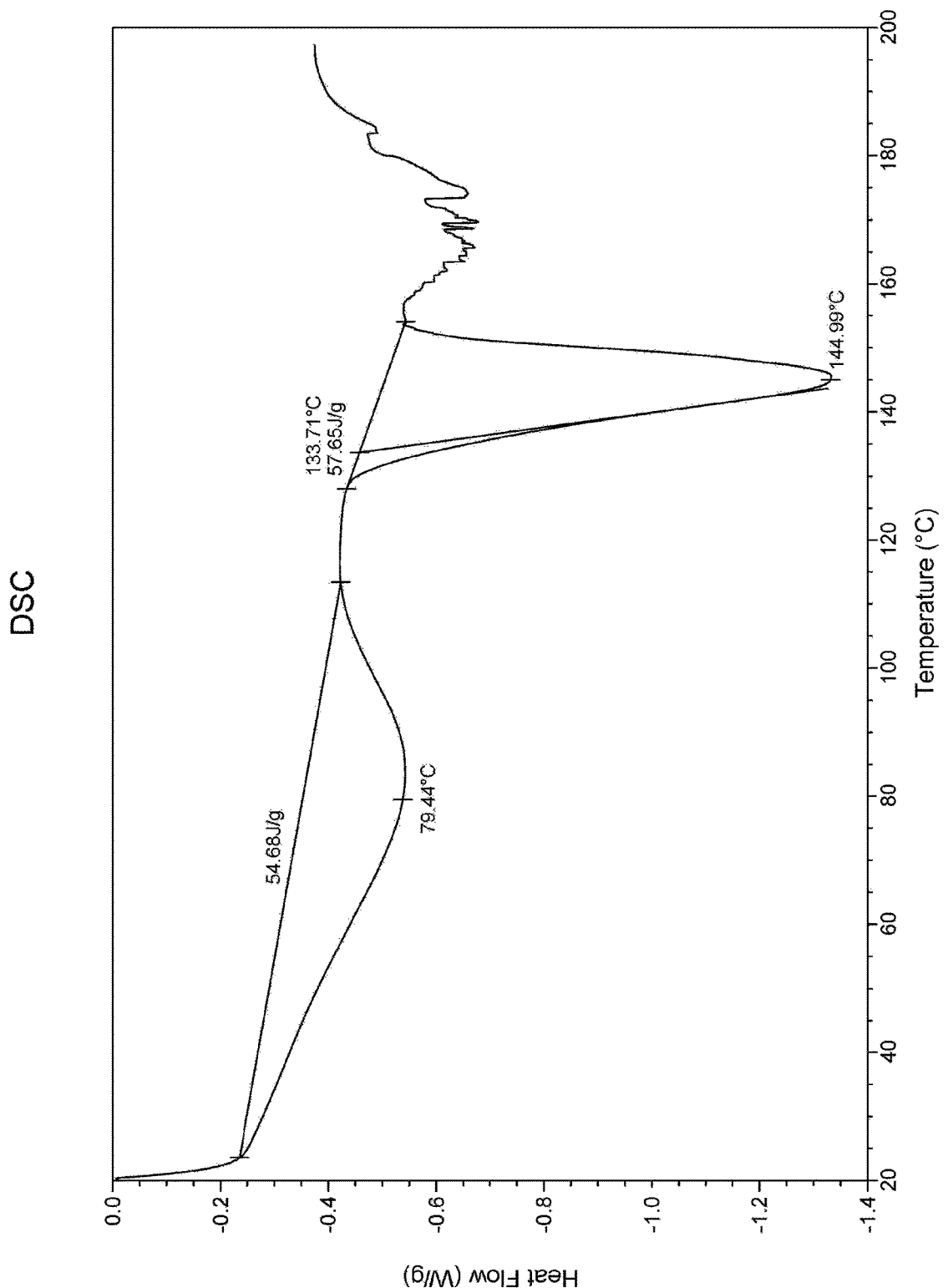
FIG. 24 is a DSC plot of the morpholine derivative hydrochloride.

The morpholine derivative hydrochloride exhibits a Differential Scanning Calorimetry (DSC) plot as shown in FIG. 24, and the DSC plot shows a very broad endothermic peak (57.68 J/g) between 25 and 115° C., and an endothermic peak (57.65 J/g) at 133° C.

Figure 25:
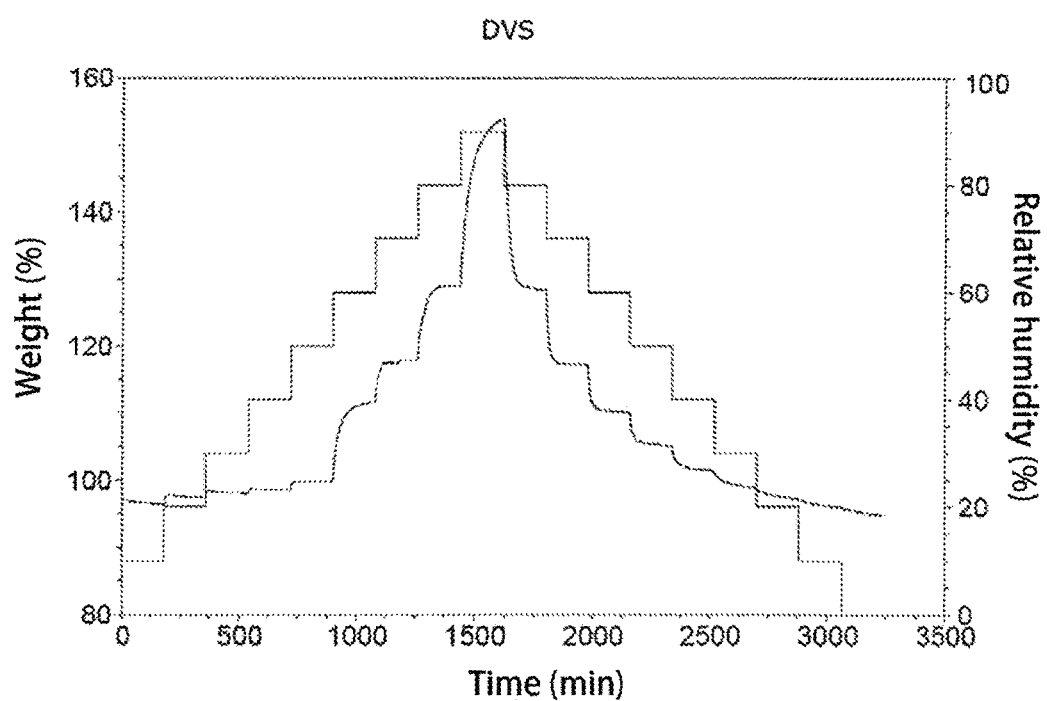
FIG. 25 is a DVS plot of the morpholine derivative hydrochloride.

The morpholine derivative hydrochloride exhibits a Dynamic Vapor Sorption Analysis (DVS) plot as shown in FIG. 25, and the DVS plot shows that the morpholine derivative hydrochloride absorbs 15% of water in 0% to 60% RH, and it is deliquescent in this humidity range.

Example 6

Preparation of the Morpholine Derivative Acetate 10.64 mg (0.024 mmol, 1 eq) of the free base was dissolved in 0.4 ml of acetone, 2.03 mg (0.033 mmol, 1.4 eq) of acetic acid was dissolved in 0.1 ml of acetone, and then the formulated solution of acetic acid in acetone was added dropwisely to the solution of the free base in acetone. The mixture was stirred overnight at room temperature to precipitate a white solid that was filtered and characterized.

Figure 26:
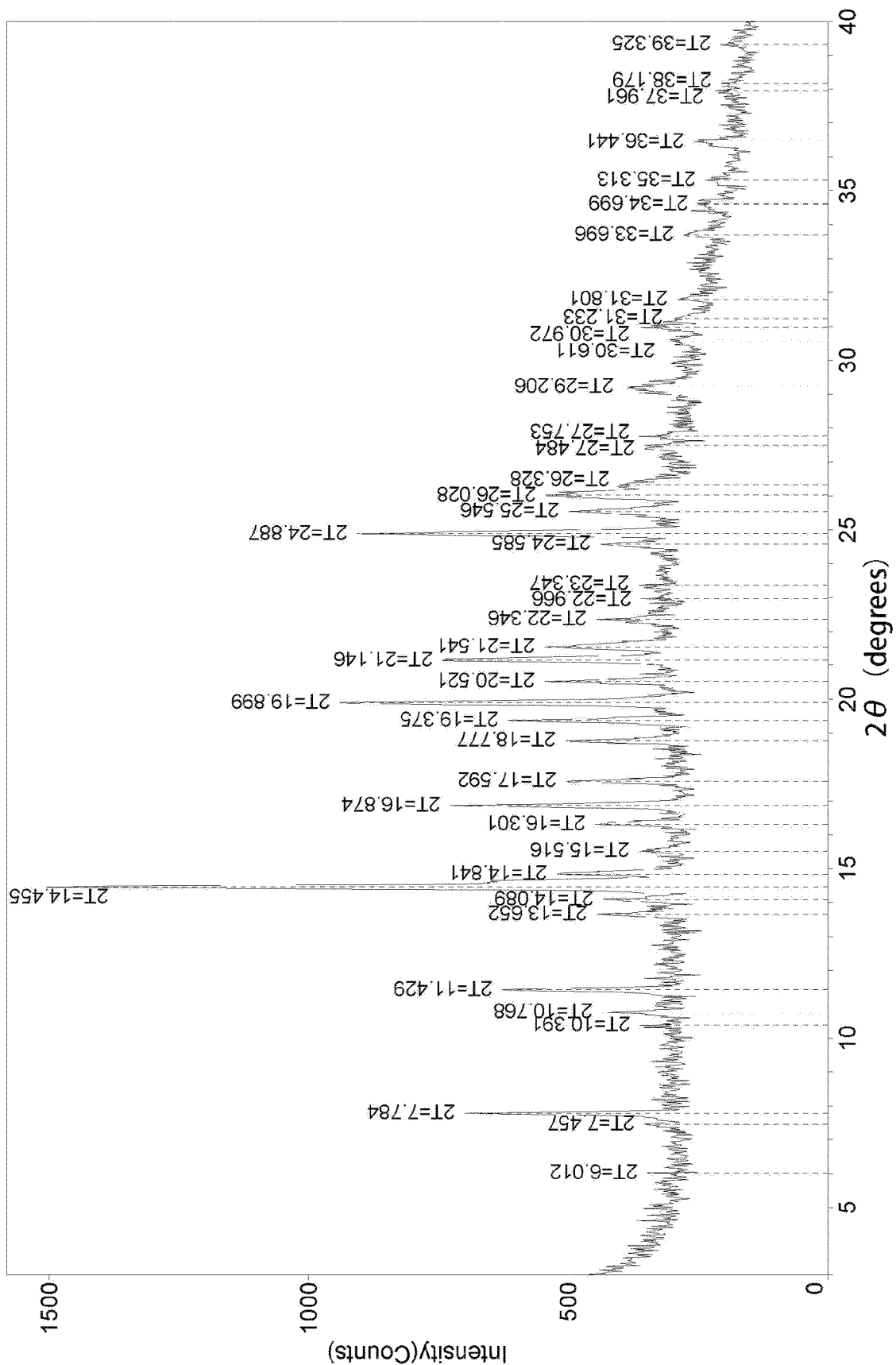
FIG. 26 is an XRPD pattern of the morpholine derivative acetate.

The morpholine derivative acetate exhibits an X-ray Powder Diffraction (XRPD) pattern as shown in FIG. 26.

Figure 27:
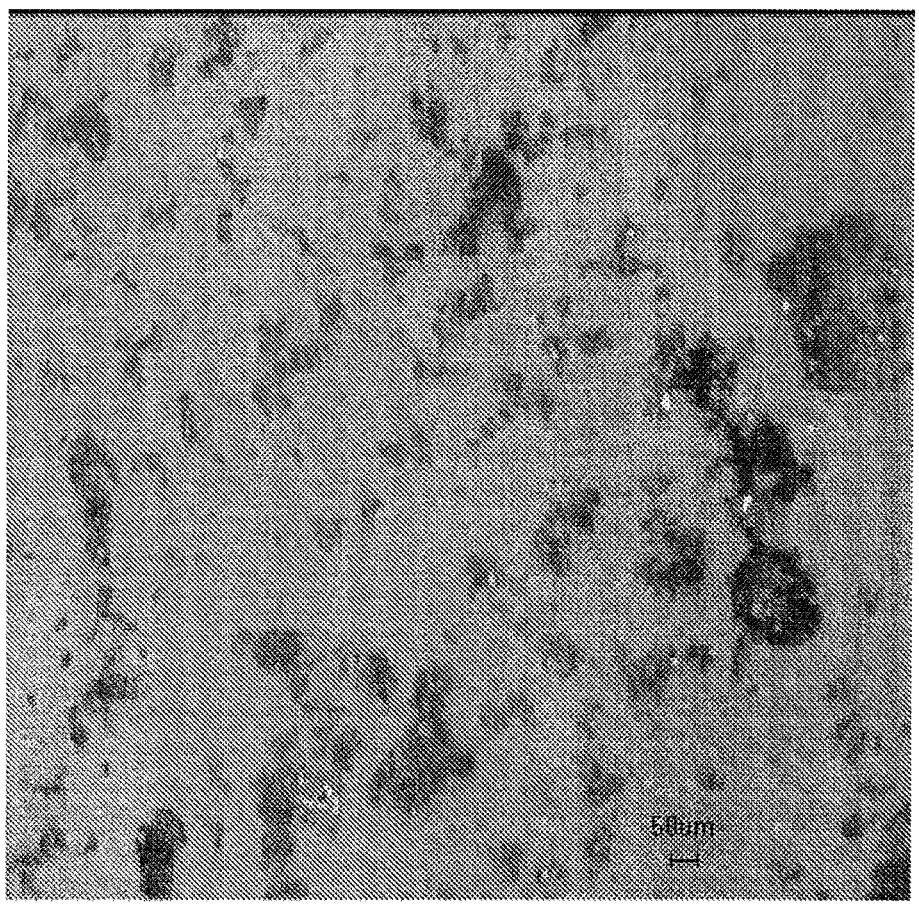
FIG. 27 is a PLM image of the morpholine derivative acetate.

The morpholine derivative acetate exhibits a Polarized Light Microscopy (PLM) image as shown in FIG. 27.

Figure 28:
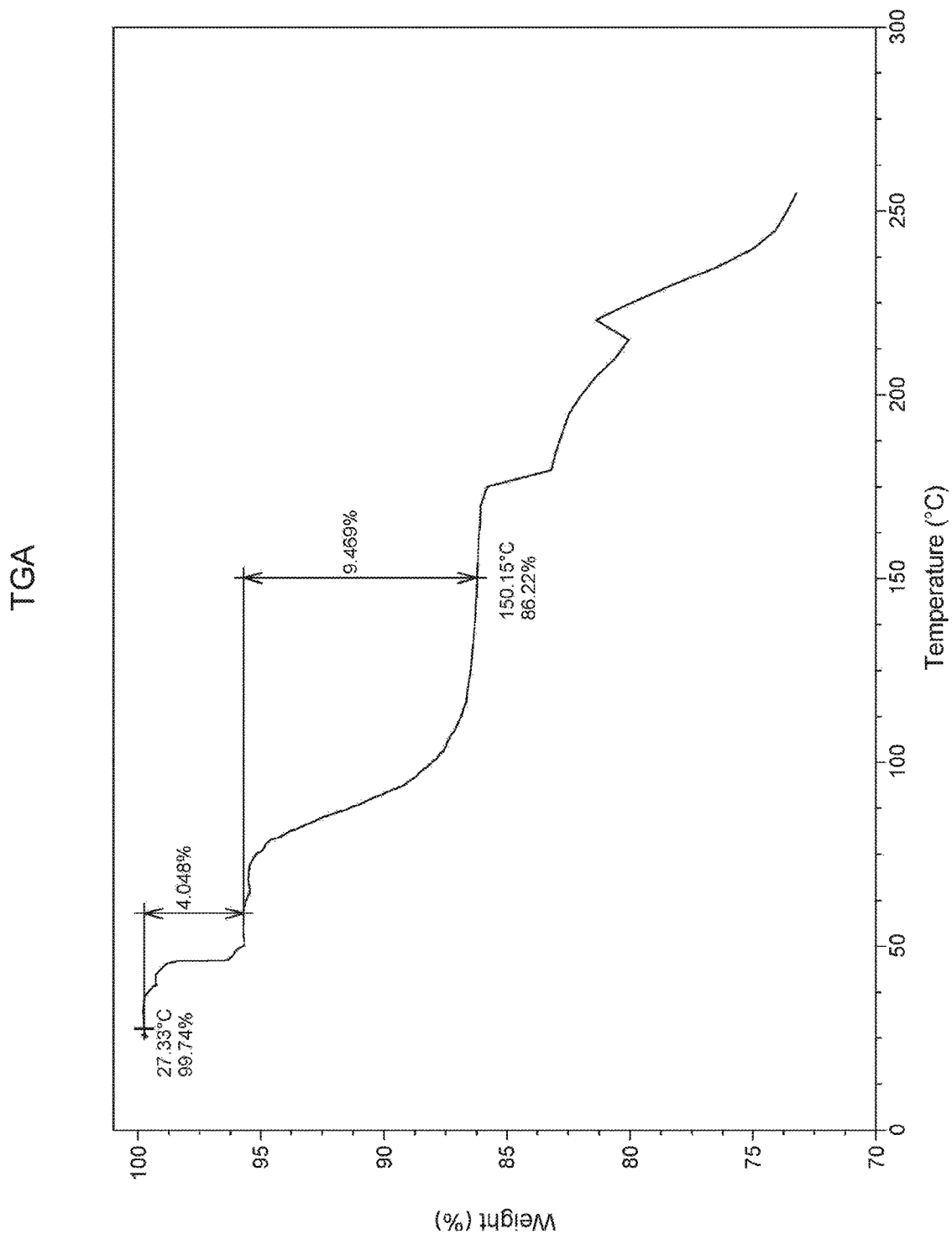
FIG. 28 is a TGA plot of the morpholine derivative acetate.

The morpholine derivative acetate exhibits a Thermogravimetric Analysis (TGA) plot as shown in FIG. 28, the TGA plot shows that the morpholine derivative acetate has a stepwise weight loss of 4.0% and 9.5% each at about 50° C. and 75° C., respectively.

Figure 29:
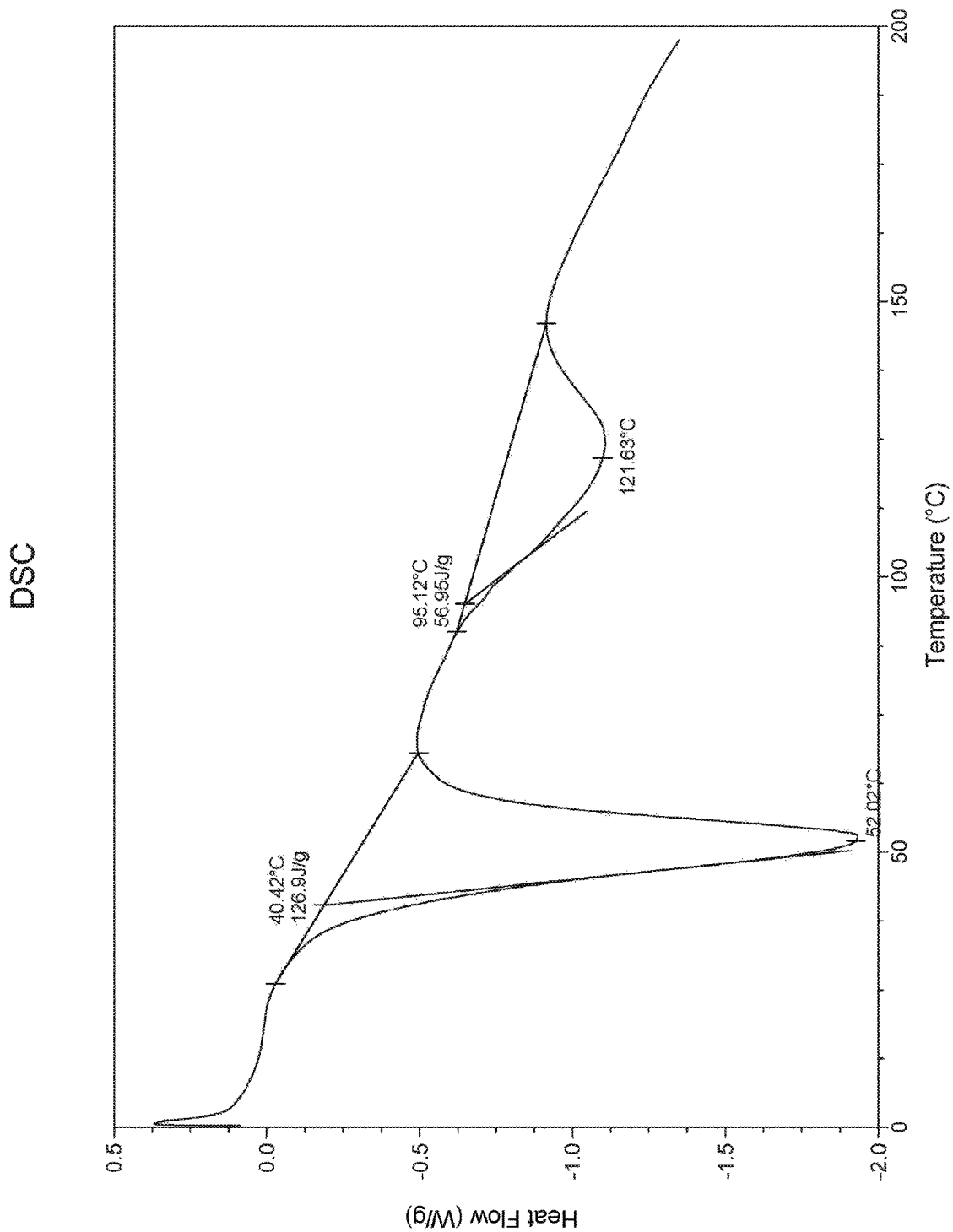
FIG. 29 is a DSC plot of the morpholine derivative acetate.

The morpholine derivative acetate exhibits a Differential Scanning Calorimetry (DSC) plot as shown in FIG. 29, and the DSC plot shows an endothermic peak (61 J/g) at 95° C.

Figure 30:
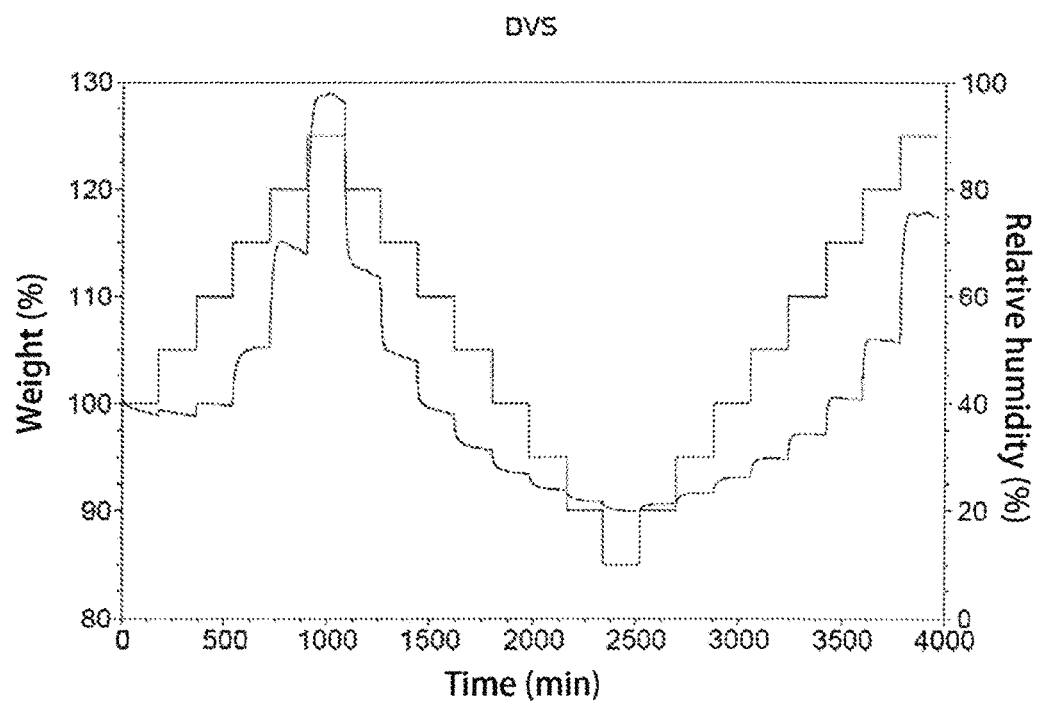
FIG. 30 is a DVS plot of the morpholine derivative acetate.

The morpholine derivative acetate exhibits a Dynamic Vapor Sorption Analysis (DVS) plot as shown in FIG. 30, and the DVS plot shows that the morpholine derivative acetate loses about 5% of the weight during the drying stage at 0% of the initial humidity, and then it absorbs moisture in an amount of 6.4% of its weight in a range of 20% to 60% humidity, and absorbs moisture in an amount of 40% of its weight at 90% of humidity, indicating that it is deliquesced.

Example 7

Preparation of the Naphthalene Disulfonate 10.68 mg (0.024 mmol, 1 eq) of the free base was dissolved in 2 ml of ethyl acetate, and 12.17 mg (0.034 mmol, 1.4 eq) of naphthalene disulfonic acid was dissolved in 1 ml of ethanol, and then the formulated solution of naphthalene disulfonic acid in ethanol was added dropwisely to the solution of the free base in ethyl acetate. The mixture was stirred to give a white flocculent precipitate that was filtered and characterized.

Figure 31:
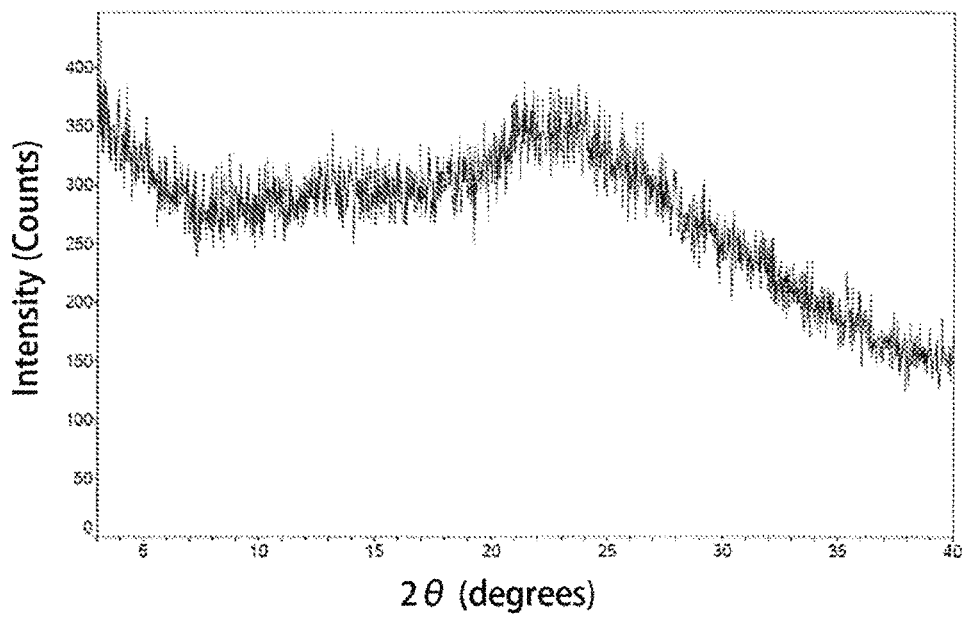
FIG. 31 is an XRPD pattern of the morpholine derivative naphthalene disulfonate.

The morpholine derivative naphthalene disulfonate exhibits an X-ray powder diffraction (XRPD) pattern as shown in FIG. 31, and it is an amorphous salt.

Test Example 1

Solubility Test 5 mg of each of the free base and salts of the morpholine derivative in Examples 1-7 was added with pure water gradually at 25° C., until all the samples were completely dissolved. The solubility of each sample was calculated based on the actual weight of the sample and the amount of water. The results are shown in Table 1. Parallel test shows that no crystal transformation occurred in the sample during this test.

TABLE 1

Solubility Tests for Various Salts of Morpholine Derivative

| Sample | Solubility (mg/ml) |
| --- | --- |
| morpholine derivative malate | 100 |
| morpholine derivative tartrate crystal form B | 150-300 |
| morpholine derivative tartrate dihydrate | 100 |
| morpholine derivative tartrate crystal form A | 100 |
| morpholine derivative hydrochloride | >500 |
| morpholine derivative acetate | 150-300 |
| morpholine derivative naphthalene disulfonate | >500 |
| morpholine derivative free base | 5-10 |

Test Example 2

Stability Test 5 mg of each of the salts of the morpholine derivative in the examples was measured for their weight change as the humidity was increased from 20% to 80%. The results are shown in Table 2.

TABLE 2

Hygroscopicity Tests for Various Salts of Morpholine Derivative

| Sample | Weight change in 20%-80% humidity | Level |
| --- | --- | --- |
| morpholine derivative malate | 1.70% | difficult |
| morpholine derivative tartrate crystal form B | 6.58% | easy |
| morpholine derivative tartrate dihydrate | 9.05% | easy |
| morpholine derivative tartrate crystal form A | 1.50% | difficult |
| morpholine derivative hydrochloride | 31.80% | Very easy |
| morpholine derivative acetate | 21.30% | Very easy |
| morpholine derivative naphthalene disulfonate | N/A | Very easy |
| morpholine derivative free base | N/A | difficult |

Note:
N/A means not available.

The stability test was conducted on 10 mg of each of the free base and salts of the morpholine derivative in the examples under oxidation condition. The results are shown in Table 3.

TABLE 3

Stability tests for various salts of morpholine derivative under oxidation condition

| Sample | The decomposed amount (%) | Types of new impurities (type) |
| --- | --- | --- |
| morpholine derivative malate | 8.46% | 2 |
| morpholine derivative tartrate crystal form B | 3.24% | 4 |
| morpholine derivative tartrate crystal form A | 17.93% | 6 |
| morpholine derivative free base | 38.0% | 6 |
| morpholine derivative naphthalene disulfonate | 51.47% | 7 |
| morpholine derivative hydrochloride | 63.53% | 6 |
| morpholine derivative acetate | 95.71% | 5 |
| morpholine derivative tartrate dihydrate | N/A | N/A |

Note:

N/A means not available.

*Oxidation condition: a watch glass, in which an appropriate amount of raw material was placed in a thickness of about 3-5 mm, was placed in a closed container containing hydrogen peroxide urea in a 40° C. environment for 12 days, and then the raw material was sampled for solid-state characterization and chiral HPLC to determine the amount of the sample. The results are compared with the amount of the sample on day 0.

The stability test was carried out on 10 mg of each of the free base, salts of the morpholine derivative in Examples 1-6 under light condition. The results are shown in Table 4.

TABLE 4

Stability Tests for Various Salts of Morpholine Derivative under light condition

| Sample | The decomposed amount (%) |
| --- | --- |
| morpholine derivative malate | 2.05% |
| morpholine derivative tartrate crystal form B | 3.61% |
| morpholine derivative tartrate crystal form A | 2.14% |
| morpholine derivative hydrochloride | 5.27% |
| morpholine derivative acetate | 100% |
| morpholine derivative naphthalene disulfonate | 12.58% |
| morpholine derivative free base | 100% |

*Light condition: An appropriate amount of raw material was spread in a thickness of 3-5 mm in a watch glass, then the watch glass was placed in a light box with an illumination of 4500 Lx ± 500 Lx (25° C.) for 12 days, and then the raw material was sampled for solid characterization, chiral HPLC to determine the amount of the sample. The results are compared with the amount of the sample on day 0.

The above detailed embodiments of the present invention are presented only for illustrating purpose, and the protection scope of the present invention is not limited thereto. All the changes or alternatives that may be made by a person skilled in the art without creative labor within the technical scope disclosed by the present invention shall be included in the protection scope of the present invention.

The invention claimed is:

1. A morpholine derivative malate, wherein the morpholine derivative malate is a compound formed by a morpholine derivative and L-malic acid in a molar ratio of 1:1, and represented by the following structural formula:

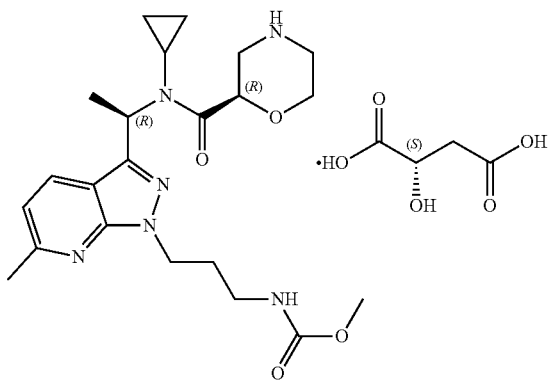

wherein the morpholine derivative malate is a crystal form having characteristic peaks at 2θ of 7.767°±0.2°, 13.897°±0.2°, 14.775°±0.20° 17.098°±0.20° 18.999°±0.2° 20.153°±0.2° 20.960°±0.2°, 21.423°±0.2°, 26.348°±0.2°, 27.892°±0.2° in the X-ray powder diffraction pattern.

2. The morpholine derivative malate of claim 1, wherein the crystal form further has characteristic peaks at 2θ of 5.598°±0.2°, 7.357°±0.2°, 10.395°±0.2°, 11.108°±0.2°, 16.037°±0.2°, 16.523°±0.2°, 19.410°±0.2°, 22.645°±0.2°, 26.630°±0.2°, 26.891°±0.2°, 27.380°±0.2°, 31.056°±0.2°, 33.306°±0.2°, 33.775°±0.2°, 39.231°±0.2° in the X-ray powder diffraction pattern.

3. The morpholine derivative malate of claim 1, wherein the crystal form exhibits an X-ray Powder Diffraction pattern as shown in FIG. 1.

4. A morpholine derivative tartrate, wherein, the morpholine derivative tartrate is a compound formed by a morpholine derivative and L-tartaric acid in a molar ratio of 1:1, and represented by the following structural formula:

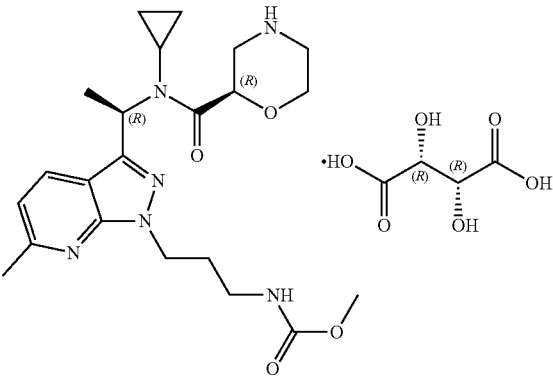

wherein the morpholine derivative tartrate is a morpholine derivative tartrate crystal form B, which has characteristic peaks at 2θ of 3.339°+0.2°, 6.562°+0.2°, 11.331°+0.2°, 16.396°+0.2°, 22.041°+0.2° in the X-ray powder diffraction pattern.

5. The morpholine derivative tartrate of claim 4, wherein, the crystal form B further has characteristic peaks at 2θ of 5.078°±0.2°, 6.864°±0.2°, 8.250°±0.2°, 8.444°±0.2°, 11.030°±0.2°, 12.864°±0.2°, 13.907°±0.2°, 14.642°±0.2°, 19.100°±0.2°, 19.359°±0.2°, 25.251°±0.2°, 26.768°±0.2°, 27.894°±0.2°, 29.510°±0.2°, 38.343°±0.2° in the X-ray powder diffraction pattern.

6. The morpholine derivative tartrate of claim 4, wherein, the morpholine derivative tartrate crystal form B exhibits an XRPD pattern as shown in FIG. 6.

7. A dihydrate of the morpholine derivative tartrate of claim 4, wherein, the dihydrate has characteristic peaks at 2θ of 9.851°±0.2°, 14.410°±0.2°, 14.774°±0.2°, 15.052°±0.2°, 16.254°±0.2°, 20.847°±0.2°, 23.225°±0.2° in the X-ray powder diffraction pattern.

8. The dihydrate of the morpholine derivative tartrate of claim 7, wherein, the dihydrate further has characteristic peaks at 2θ of 13.434°±0.2°, 15.415°±0.2°, 15.701°±0.2°, 16.755°±0.2°, 17.283°±0.2°, 18.079°±0.2°, 18.576°±0.2°, 20.077°±0.2°, 21.960°±0.2°, 24.351°±0.2°, 27.046°±0.2°, 27.865°±0.2°, 38.458°±0.2° in the X-ray powder diffraction pattern.

9. The dihydrate of the morpholine derivative tartrate of claim 7, wherein, the dihydrate exhibits an XRPD pattern as shown in FIG. 11.

10. A tetrahydrate of the morpholine derivative tartrate of claim 4, wherein, the tetrahydrate is a morpholine derivative tartrate crystal form A having characteristic peaks at 2θ of 9.882°±0.2°, 14.426°±0.2°, 14.802°±0.2°, 16.275°±0.2°, 20.085°±0.2°, 20.872°±0.2°, 21.978°±0.2°, 23.236°±0.2° in the X-ray powder diffraction pattern.

11. The tetrahydrate of the morpholine derivative tartrate of claim 10, wherein, the crystal form A further has characteristic peaks at 2θ of 11.964°±0.2°, 13.558°±0.2°, 15.076°±0.2°, 15.450°±0.2°, 16.046°±0.2°, 16.754°±0.2°, 17.320°±0.2°, 18.450°±0.2°, 18.790°±0.2°, 19.728°±0.2°, 20.577°±0.2°, 22.426°±0.2°, 23.704°±0.2°, 24.399°±0.2°, 25.346°±0.2°, 25.913°±0.2°, 26.991°±0.2°, 28.199°±0.2°, 28.445°±0.2°, 29.030°±0.2°, 30.209°±0.2°, 30.480°±0.2°, 32.791°±0.2°, 34.796°±0.2°, 36.226°±0.2°, 38.472°±0.2° in the X-ray powder diffraction pattern.

12. The tetrahydrate of the morpholine derivative tartrate of claim 10, wherein, the tetrahydrate exhibits an XRPD pattern as shown in FIG. 16.

13. The morpholine derivative malate of claim 2, wherein the crystal form exhibits an X-ray Powder Diffraction pattern as shown in FIG. 1.

14. The morpholine derivative tartrate of claim 5, wherein, the morpholine derivative tartrate crystal form B exhibits an XRPD pattern as shown in FIG. 6.

15. The dihydrate of the morpholine derivative tartrate of claim 8, wherein, the dihydrate exhibits an XRPD pattern as shown in FIG. 11.

16. The tetrahydrate of the morpholine derivative tartrate of claim 11, wherein, the tetrahydrate exhibits an XRPD pattern as shown in FIG. 16.

* * * * *